United States Patent [19]

Descales et al.

[11] Patent Number: 5,763,883
[45] Date of Patent: Jun. 9, 1998

[54] CHEMICALS PROPERTY DETERMINATION

[75] Inventors: Bernard Descales, Marseilles; Didier Lambert, Saint-Mitre-Les-Remparts; Jean-Richard Llinas, Marseilles; Andre Martens, Chateauneuf-Les-Martigues, all of France

[73] Assignees: BP Chemicals Limited; BP Oil International Limited, both of London, England

[21] Appl. No.: 467,179

[22] Filed: Jun. 6, 1995

[30] Foreign Application Priority Data

Oct. 7, 1994 [EP] European Pat. Off. ............ 94430010

[51] Int. Cl.$^6$ ................................................. G01N 31/08
[52] U.S. Cl. ........................ 250/339.09; 250/339.12; 250/341.5
[58] Field of Search .................. 250/339.09, 339.12, 250/340, 341.1, 341.5; 364/498

[56] References Cited

U.S. PATENT DOCUMENTS

| | | | |
|---|---|---|---|
| 3,896,312 | 7/1975 | Brown et al. | 250/343 |
| 3,997,786 | 12/1976 | Lauer et al. | |
| 4,251,870 | 2/1981 | Jaffe . | |
| 4,766,551 | 8/1988 | Begley . | |
| 4,882,755 | 11/1989 | Yamada et al. | |
| 5,023,804 | 6/1991 | Hoult . | |
| 5,082,985 | 1/1992 | Crouzet et al. | |
| 5,121,337 | 6/1992 | Brown | 364/498 |
| 5,153,140 | 10/1992 | Langfeld et al. | |
| 5,225,679 | 7/1993 | Clarke et al. | |
| 5,262,961 | 11/1993 | Farone . | |
| 5,311,445 | 5/1994 | White . | |
| 5,361,912 | 11/1994 | Krieg et al. | |
| 5,446,681 | 8/1995 | Gethner et al. | |
| 5,452,232 | 9/1995 | Espinosa et al. | |
| 5,475,612 | 12/1995 | Espinosa et al. | |

FOREIGN PATENT DOCUMENTS

| | | |
|---|---|---|
| 304232 | 2/1989 | European Pat. Off. . |
| 305090 | 3/1989 | European Pat. Off. . |
| 437829 | 7/1991 | European Pat. Off. . |
| 607048 | 7/1994 | European Pat. Off. . |
| 625702 | 11/1994 | European Pat. Off. . |
| 631810 | 1/1995 | European Pat. Off. . |
| 2626579 | 8/1989 | France . |
| WO92/07326 | 4/1992 | WIPO . |

OTHER PUBLICATIONS

"Selection of Samples for Calibration in Near–Infrared Spectroscopy. Part II: Selection Based on Spectral Measurements"; *Applied Spectroscopy;* vol. 44, No. 7; T. Isaksson and T. Naes; pp. 1152–1158; ©1990.

"Nonlinear Multicomponent Analysis by Infrared Spectrophotometry"; *Analytical Chemistry;* vol. 55; M. Maris and C. Brown; pp. 1624–1702; ©1983.

(List continued on next page.)

*Primary Examiner*—David P. Porta
*Assistant Examiner*—Richard Hanig
*Attorney, Agent, or Firm*—Fay, Sharpe, Beall, Fagan, Minnich & McKee

[57] ABSTRACT

A method of determining or predicting a value $P_x$ of a property of a material X, which is a feed to a process or a property of a product of a process from said material or yield of said process, which method comprises measuring the absorption $D_ix$ of said material at more than one wavelength in the region 600–2600 nm, comparing the said absorptions or a derivative thereof with absorptions $D_im$ or derivatives thereof at the same wavelength for a number of standards S in a bank for which the said property or yield P is known, and choosing from the bank at least one standard $S_m$ with property $P_m$ said standard having the smallest average value of the absolute difference at each wavelength i between the absorption $D_ix$ (or derivative thereof) for the material and the absorption $D_im$ (or derivative thereof) for the standards $S_m$ to obtain $P_x$, with averaging of said properties or yields $P_m$ when more than one standard $S_m$ is chosen, and wherein said process is at least one of polymerization, an oligomerization or an organic reaction in which at least one of the reactant and a product is a functionalized compound.

17 Claims, 2 Drawing Sheets

OTHER PUBLICATIONS

"Near–Infrared Spectrum Qualification via Mahalanobis Distance Determination"; *Applied Spectroscopy*; vol. 41, No. 7; R. G. Whitfield et al.; pp. 1204–1213; ©1987.

"Unique Sample Selection via Near–Infrared Spectral Subtraction" (*Analytical Chemistry*; vol. 57; No. 12; D. E. Honigs et al.; pp. 2299–2303; ©1985).

"Selection of Calibration Samples for Near–Infrared Spectrometry by Factor Analysis of Spectra" (*Analytical Chemistry*; vol. 60; No.6; G. Puchwein; pp. 569–573; ©1988.

"The Design of Calibration in Near Infra–Red Reflectance Analysis by Clustering" (*Journal of Chemometrics*; vol. 1; T. Naes; pp. 121–126 ©1987.

"Multicomponent Analysis of FT–IR Spectra" (*Applied Spectroscopy*; vol. 45; No. 6; P. Saarinen and J. Kauppinen; pp. 953–963; ©1991.

"Computer Searching of Infrared Spectra Using Peak Location and Intensity Data" (*Analytical Chem.*; vol. 48, No.4; R. C. Fox; pp. 717–721; ©1976).

"On–line NIR Analysis and Advanced Control Improve Gasoline Blending" (*Oil Gas J.*; vol.92; No.42; A. Espinosa et al.; pp. 49–56; ©1994.

"Online Process Analyzers" (*Chemical Engineering*; vol.83; No. 13; V.C. Utterback; pp. 141–144; ©1976.

CHEMICALS PROPERTY DETERMINATION

BACKGROUND OF THE INVENTION

This invention relates to a method of determining or predicting by near infra red (NIR) spectroscopy properties of feeds or products and/or yields in chemical processes including polymerisation.

NIR spectroscopy has many advantages over other methods of analysis and can cover a large number of repetitive applications accurately, quickly and on line. The NIR region between 800 and 2500 nm contains the totality of molecular information in the form of combinations and overtones from polyatomic vibrations, but Mathematical techniques are needed to exploit this information and to calculate the desired parameters. U.S. Pat. No. 5,490,085 (issued Feb. 6, 1996), U.S. Pat. No. 5,452,232 (issued Sep. 19, 1995), and U.S. Pat. No. 5,475,612 (issued Dec. 12, 1995), the disclosure of which is hereby incorporated by reference, describe the use of NIR for determining octane number, yields and/or properties of a product of a chemical process in a refinery or separation process from analysis on the feeds to that process, and yields and/or properties of a product of a blending operation again from analysis on the feed thereto.

At present, numerical methods described for modelling physicochemical properties based on NIR spectra all are of a correlative nature and involve relations of a regressional character between the property(ies) studied. Among these multivariable analyses are multilinear regression (MLR), Principle Component Regression (PLR), Canonic regression, and regression by Partial Least Squares (PLS). In all cases there is sought between the property and the NIR spectrum a relation which may be linear but is usually quadratic or of higher algebraic form involving regression coefficients applied to each absorption. The establishment of any regression requires a progressive calibration, as the approach is empirical and not supported by a theory.

These techniques have disadvantages, the chief of which is the need for establishing a strong correlation between the spectrum and the property, and their difficulty in dealing with positive or negative synergy between components contributing to that property. In the case of high density polyethylene one multi linear regression model in respect of density gives a coefficient of correlation that can on occasion be insufficiently high, so as to give problems in a polymerization process based on it.

Furthermore there are practical difficulties mainly in the need to identify sample families having the same kind of relation between the spectrum and the properties to be modelled. Thus the model may be limited especially with a non linear relation between spectrum and property. Especially when at the edges of the available data the accuracy of the model diminishes. The stability of the model is also a problem, as is the need when adding new standards to do laborious revisions to give the new model, especially when adjusting to a new feedstock for a process; thus testing 6 properties on 4 products leaving a process requires 24 models, each of which has to be changed for each change of the feed not included in the calibration.

We have discovered a new approach avoiding the above problems with correlations, and regression calculations, and being capable of being expanded automatically with use of a new product of different quality.

SUMMARY OF THE INVENTION

The present invention provides a method of determining or predicting a value Px, of a property of a material x which is a feed to a process or a property of a product of a process from said material or yield of said process which method comprises measuring the absorption ($D_i m$) of said material at more than one wavelength in the region 600–2600 nm, comparing the said absorptions or a derivative thereof with absorptions $D_i x$ or derivatives thereof at the same wavelengths for a number of standards S in a bank for which the said property or yield P is known, and choosing from the bank at least one, and preferably at least 2 standard $S_m$ with properties or yield $P_m$, said standard Sm having the smallest average value of the absolute difference at each wavelength i between the absorption $D_i x$ (or derivative thereof) for the material and the absorption $D_i m$ (or derivative thereof) for the standard $S_m$ to obtain value $P_m$ with averaging of said properties or yield Pm, when more than 1 standard $S_m$ is chosen, and wherein standard $S_m$ and to obtain the value $P_x$ and with averaging of said properties of yields $P_m$ when more than one standard $S_m$ is chosen and wherein said process is at least one of a polymerization, an oligomerization or an organic reaction in which at least one of the reactant and a product is a functionalized compound.

The above method can be performed without regression or correlation techniques.

DETAILED DESCRIPTION

Figure 1:
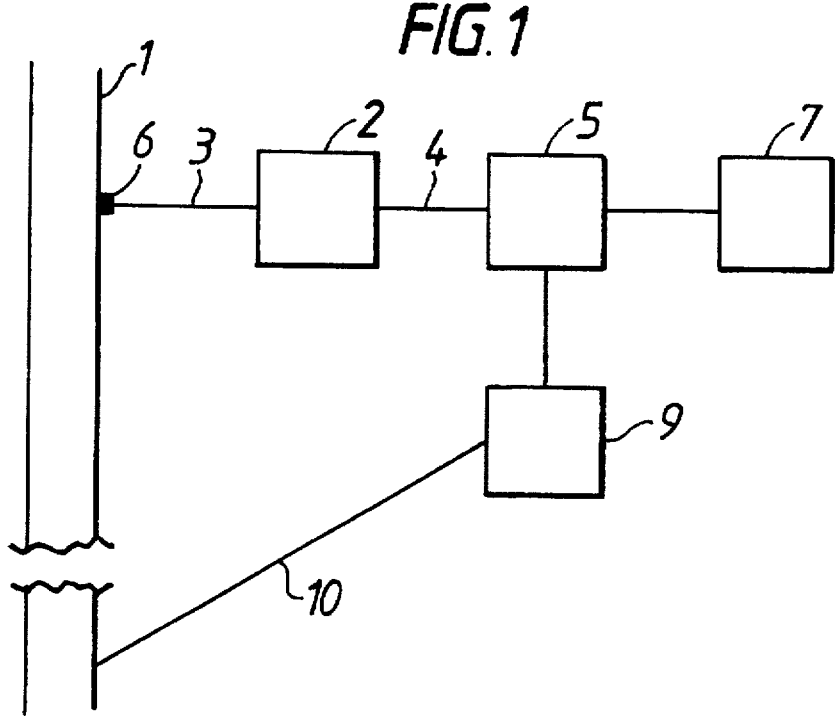
FIG. 1 represents a schematic diagram showing apparatus for use in the invention.

In FIG. 1, an optical fibre of tube 3 links a spectrometer 2 and a probe 6 in or at process line 1. The spectrophotometer 2 produces absorbance signals at more than 1 wavelength, which signals are passed via line 4 to computer 5, where the signals as such or after conversion to one or more derivative signals, are used to enable the computer to access the databank 7 of standard absorptions and properties/yields therein. The signals are compared to those of the standard absorptions as described above and one or more standard absorption(s) and its/their corresponding property(ies) or yield(s) The output of the computer 5 may be in the form of spectral absorbancies or a property or yield of the product in line 1 and may be printed in hard copy. Preferably however, the output as a signal is used to control the process involved with the product in line 1, ie for which line 1 is a feed or a product line; in this case the computer 5 is linked to and instructs the controller 9 which, via line 10, controls that process by acting on operating conditions eg. via valves/temperature and/or pressure controls in line 1 or in relation to line 1. By this means the property or yield of product in line 1 can be optimised.

Figure 2:
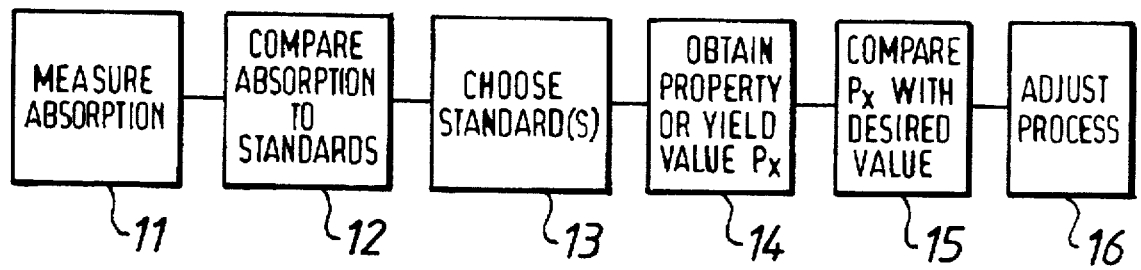
FIG. 2 represents a schematic block flow diagram for the method of the invention.

In FIG. 2, the initial operation 11 is to measure the absorption of the unknown, after which in the second step 12, the absorptions are compared to absorptions in spectra of standards, and in the third step 13, the spectra of the standards Sm are chosen according to criteria described above, and then in step 14, the property(ies) of the standard (s) Sm chosen is used to obtain the desired property or yield. If the spectrum of only 1 standard Sm is chosen, then the value $P_x$ of the unknown is the same as that of that standard Pm. If more than 1 spectrum is chosen, the value $P_x$ of the unknown is the average of the values Pm of the standards. If desired in an optional step 15, the value $P_x$ is compared to the desired value for the unknown and in step 16 the process involving the unknown is adjusted to make the value $P_x$ the same as the desired value.

Thus for the performance of the method of the invention, a bank is prepared in which the NIR spectra are recorded at many wavelengths for a large number of standard materials, together with their properties (or those of products obtained by the above processes therefrom) determined by alternative techniques e.g. gaschromatography for chemical compositions or yields determined by known method. The standards are chosen to cover the area in which the method is to be used, so for determination of properties of polyethylenes, a range of polyethylenes is chosen of widely varying properties, with different contents of comonomer, or other properties such as molecular weight. The number of wavelengths chosen may be 2–1000 e.g. 5–100 or 10–80 such as 25–65, while the number of standards can be at least 100 or 1000, or 100.000 up to 5 million depending on property(ies) chosen.

The wavelengths chosen may be at regular intervals such as each 10–50 or 15–35 nm (or each 1–5 nm or each nanometer) or may be at irregular intervals e.g. with intervals of 1–100 nm such as 2–50 nm which may be random or chosen because of a change in the shape of the spectral curve at that wavelength e.g. a peak, trough or shoulder. The wavelength may be in the region for 600–2500 nm, eg 900–2500 nm such as 1000–2000 nm, while the wavelengths may be 16.600–4000 $cm^{-1}$ such as 11000–4000, 10000–5000 $cm^{-1}$; frequencies in Hertz are obtained by multiplying the wave numbers by $3 \times 10$ cm/sec.

The absorptions for the unknown sample are compared with the absorptions at the same wavelength of the standards, and those standards chosen having the smallest differences. The properties of those chosen standards are then averaged to determine the property of the unknown sample. The absorptions at more than one wavelength may be chosen, e.g. 2–1000 such as 5–100 or 10–20

In the method of the invention the standards chosen are those with the smallest average values of the absolute difference at each wavelength i between the absorption/optical density (or a derivative thereof) $D_{ix}$ for the unknown material and the corresponding absorption/optical density (or derivative thereof) $D_{im}$ for the standard. The averages may be in respect of the mean value of $D_{ix}-D_{im}$ (whatever its sign ie the absolute difference), or $(D_{ix}-D_{im})^2$ and may be the simple mean value or the differences may be weighted to take account of the different sensitivity of the absorption to the property at that wavelength or the different sensitivity of the spectrometer at that wavelength. For each standard in the bank of standards for the type of material in question, the average difference is found as described and the smallest average differences chosen, e.g. at least 1 preferably at least 2 such as up to 1000 smallest such as 1 or 2–100 or 1 or 2–20 but inparticular 1–10 and especially 2–6 smallest. Advantageously the average differences chosen and hence the standard (or standards) $S_m$ chosen for the property or yield wanted are such that in relation to the unknown material X and each chosen standard/$S_m$ the following function is met $$\frac{i_{xm}}{\Sigma D_{ix}} < \text{experimental error}$$

wherein $i_{xm}$ is the proximity index and is defined by $i^2(xm)=\Sigma (D_ix-D_im)^2$ and the experimental error is in determining said property or yield in the standard. The value $P_x$ of the property or yield is the same as $P_m$ or the average of $P_m$ when more than one standard $S_m$ is chosen.

In order to aid the choice of the appropriate standards, especially in relation to a large number of wavelengths for a complex unknown mixture, it is preferred to limit the choice to those defined by means of a minimal index. For the chosen standard the minimal index is at least the same as the differences between the absorptions of the unknown and the standards. Mathematically, this may be expressed as $i^2ab \leq i^2M$ where iM is the minimal index for the property, and iab is a measure of the deviation (called the proximity index) at all the chosen wavelengths between absorption of the unknown and a chosen standard b. That measure is defined by $$i(ab)^2=\Sigma_i (D_{ia}-D_{ib})^2 \quad (1)$$

where $D_{ia}$ is the optical density (or absorbence) of unknown a at wavelength i (or a derivative thereof e.g. a first, second or third derivative of that density), and $D_{ib}$ is the optical density (or absorbence) of standard b at that wavelength i (or a derivative thereof e.g. a first, second or third derivative of that density). The value of $D_i$ is the optical density or the optical density difference with respect to the baseline of the spectrum at that wavelength, or the baseline interpolated between 2 wavelengths on either side thereof.

If desired instead of the optical density $D_i$ a normalized density $W_i$ may be used where $W_i=D_i/\Sigma D_i$. This normalization avoids errors due to small electronic fluctuations in the apparatus and compensates for small differences in the optical path between the optical cells.. In this case the proximity index is defined by $$I(ab)^2=\Sigma_i (W_{ia}-W_{ib})^2 \quad (2)$$

The indices can be weighted as desired for increased resolution. One approach is to define the indices as follows.

$$I(ab)^m=\Sigma Abs\text{-}val(X_{ia}-X_{ib})^m/\sigma_i^n \quad (3)$$

where $X_i$ is $D_i$ or $W_i$ or a mathematical combination thereof, $\sigma_i$ is the standard deviation of X for the set of samples considered (at that wavelength) and each of m and n, which are the same or different is the weighting factor which is positive but can be a whole number or a fraction. Other variants can be used with other weighting factors such as those involving the spectral experimental error $e_i$, where $e_i$ is the reproducibility of the spectral measurement at wavelength i. The choice between the different options for the weighted indices may be dictated by numerical efficiency.

The reproducibility of the experimental measurements in the standards may be at least 90% or 94% or 95%. The minimal index may be obtained from a reference standard samples set according to the following procedure, hereafter called the Minimal Index Procedure. The NIR spectra for 2 standard samples A and B and their property P e.g. viscosity are determined. By means of equation (1), (2) or (3), the value of the proximity index $i_{ab}$ is determined via the absorptions at a series of wavelengths; this index is applicable to the difference in properties $P_a-P_b$ called $EP_{ab}$. This process is repeated with other pairs of standards c and d, e and f etc to obtain a series of Proximity Indices $i_{cd}$ etc with corresponding property differences $EP_{cd}$ etc. For different values of a parameter L which is greater than the indices $i_{ab}$ etc, the corresponding values of $EP_{ab}$ etc are averaged to give an average $EP_{ij}$ for that value of L; the different values of $EP_{ij}+t\sigma \sqrt{K}$ are then plotted on a graph against L. $\sigma$ is the accuracy of the property determination and K is the number of pairs of samples for which $i_{ab}$ is inferior to a given L, t is the Student factor at a given level of confidence. The intercept is then measured between the curve obtained and a line usually horizontal which is the reproducibility of the property level at an appropriate confidence interval e.g. 90% or more usually 95%. The abcissa position of the intercept gives the minimal index $i_{min}$, which is the minimum value of $i_{ab}$ for which $P_a = P_b$ within the frame of experimental error.

From this minimal index by Procedure 1, the standards can be chosen which have values of $i^2_{ab} \leq i^2_{min}$ where in this case a is the unknown and b is a standard, as in this case the difference between Property a and Property b is less than or equal to $\sigma\sqrt{2}$, where $\sigma$ is the experimental error in measuring the property. Then from the property P values of the chosen standards, the property of the unknown is obtained by averaging those values, usually the arithmetic mean, but optionally with weighting.

The method of the invention may be used to determine more than one Property P at once, e.g. at least 2, such as 1–30 e.g. 2–10 properties at once. Each property of the standards has a particular unweighted, which may lie in the region $0$–$10^{-10}$ eg $10^{-2}$ to $10^{-8}$, in particular $5 \times 10^{-7}$ to $5 \times 10^{-4}$. If the Minimal Index chosen is the smallest for all the properties desired, then the same one may be used for all the properties and the standards chosen be suitable for all the properties. The Minimal Index for each property may be used separately, with different numbers of standards chosen for each property (assuming different Minimal Indices). If desired the same Minimal Index may be used, which is not the smallest, resulting in some of the chosen standards (with a higher Minimal Index) giving some properties of high accuracy and some (with a lower Minimal Index) giving some properties of less high accuracy.

The property to be determined may be of the sample being analyzed or a product obtained from that sample e.g. a product of polymerising the sample, as the property value obtained is derived from the standards, and they will have been determined as needed for the eventual use. Our U.S. Pat. No. 5,452,232 and U.S. Pat. No. 5,475,612 referred to above describes such techniques when applied to use of NIR with correlation to blending or cracking operation; the same principles apply in the present method.

If the density of the standards in the data bank is sufficient to have $i^2_{ab} \leq i^2$ min as is usually the case, the above procedure is very satisfactory. But there are occasions when the bank is incomplete, because of shortage of data of properties in a particular area i.e. a low density of standards or the sensitivity of the property to changes in absorption is so small, that a very small Minimal Index is required and there may be few standards with proximinity indices meeting it. It is possible simply to use a larger Minimal Index with e.g. 1–5 times such as 1.5–2 times the Minimal Index; the results may be less accurate than those from a smaller Minimal Index.

However, a more accurate approach with a low density of standards involves a special densification process of Procedure 2, in which random or semi random densification of the neighbourhood of the unknown is achieved by generation of synthetic standards, based on standards already in the bank. Each new synthetic standards may be obtained from combinations of standards taken at random from the bank but preferably it is obtained from the other standards by the constraint of choosing only a mixture of N standards for which $$(\text{Min})C_j - u_j \leq C_j \leq (\text{Max})C_j + u_j \quad (4)$$

$$\text{and } \Sigma C_j = 1 \quad (5)$$

where $C_j$ is the fraction of component j in the sample $i$.

Min $C_j$ is the minimum amount of $j$ in the initial industrial calibration mixtures, or in the samples for which the method is to be used.

Max $C_j$ is the maximum amount of $j$ in the initial industrial calibration mixture or in the samples for which the method is to be used.

uj is usually between 1 and 0.01 preferably between 0.5 and 0.1 and can be fixed for each property.

The constraints over the choice of such mixtures of N standards can also be equally fixed in the spectral area from which the samples will be drawn in order to remain in the areas of similar chemical nature.

The number of samples effectively drawn into the bank in this densification can be of several thousand generally 1000–2000. The calculation time is extended without significant deterioration in the results. If no further neighbours are found, the trawl of new samples drawn in is enlarged.

The spectrum of each mixture is calculated by the combination of the spectra of the standards used according to the formula $$S_{Mi} = \Sigma\ C_{ij} \times S_j \quad (6)$$

where $S_j$ is the spectrum in the mixture of component $j$ in the calibration matrix.

The properties of each mixture PMi can be calculated by a generally linear combination of the properties of the standards according to the formula $$P_{Mi} = \Sigma\ C_{ij} \times P_j \quad (7)$$

where $P_j$ is the property of component j

In the case of non linear additive properties, appropriate mixing factors can be applied e.g. by blending factors or similar for density and viscosity.

Having obtained the spectrum and the properties of the synthetic mixtures, these can be used as "standards" to help determine the properties of an unknown sample in the same way as a conventional standard.

Instead of using either of the two above approaches, 1–7, a third type Procedure 3 may be used as follows. The Q nearest samples to unknown X can be found from a selection from the bank samples for which the proximity index to the unknown sample is $(V) \times i_{min}$ where v is $0.1 < v < 10$, (8) preferably $0.5 < v < 2$ or $1 \leq v \leq 5$. Then by the method of least squares is found a generally linear combination of the standard products (which are the Q nearest samples to reproduce the spectrum of X according to the equation.

$$S_x = \Sigma\ C_R \times S_r \quad (9)$$

where $C_r$ is the coefficient for sample R in the total Q and $S_R$ is the spectrum of sample R. The coefficient $C_R$ which can be normalized to $C_R = 1$ or not and/or optimized by the least squares route, allows an estimation of the property $P_x$ according to the equation.

$$P_x = \Sigma\ C_R \times P_R \quad (10)$$

where $P_R$ is the property of sample R.

The eventual size of the estimation error can be derived by application of Gaussian theory, also called the propagation error (see Eq.10).

The above third approach can only be applied if the product X is situated inside the maximum extension of the standard products defined by equation (8). If this is not the case, X is outside the field of the actual bank of products and escapes from the area of knowledge of the method into the area of learning.

The densification process described in relation to equations 4–7, or 9 or 10 is usually applied to the method of the invention involving no correlation or regression techniques.

However, if desired the densification process may be applied to increase the number of "standards" for consideration in an NIR analytical technique involving the correlation on regression techniques as described above e.g. MLR. The present invention also provides a method for adding an extra synthetic standard to a bank of known standards, each of which relates at least one absorption in the 600–2600 nm region (or derivative thereof) of a known material to a known property related to that material, wherein said property is of said material, which is a feed to a process, or product of said process, or yield of said process, which method comprises choosing from the bank at least 2 standards for which equations 4 and 5 above are met, considering mixing the chosen standards in at least one proportion to produce at least one mixture for use as a synthetic standard, and estimating the spectrum and property of said mixture according to equation 6 and 7 respectively, said process being at least one of a polymerization an oligomerization or an organic reaction in which at least one of the reactant and a product is a functionalized compound. The spectrum and property of each "mixture" can then be added to the bank and may be used to develop models through the known correlation/regression approach, eg based on that in the patents described above.

The method of the present invention is applicable to chemical reactions, which may be polymerisations or oligomerisations, or alternatively reactions in which at least one of a reactant and a product is a functionalised compound. In the chemical reactions each of the feeds and the products may be a solid, liquid or gas, preferably all the feeds are liquids and/or gases, and preferably all the products are liquids and/or solids, especially liquids.

Examples of polymerisations are condensation and addition polymerisation. Condensation polymerisations may produce thermoset polymers, such as phenolic novolac or resole resins curing with or without curing agents like hexamine, or polyurethanes, or thermoplastic polymers such as polyamides, e.g. polylactams such as Nylon-6 and polymers from polyamines and polycarboxylic acids e.g. poly hexamethylene adipate, and polyesters, such as those from diols e.g. aliphatic diols and organo di carboxylic acids e.g. aromatic or aryl bis (alkylene) dicarboxylic acids, such as poly ethylene terephthalate. Addition polymerisations tend to produce thermoplastic polymers, and may be thermal or free radical or catalysed reactions e.g. with Bronsted or proton acids or metals, especially transition metals. Examples of such polymerisations are those involving polymerisation at an olefinic double bond or ring opening of an epoxide or episulphide. The olefinic double bond is preferably a vinyl group $CH_2=C—$ and may be in a hydrocarbon e.g. an olefin especially an alkene such as one of 2–12 carbons especially ethylene alone or mixed with at least one alpha olefin of 3–12 carbons (especially in amount of 0.5–30% by weight based on total olefins) such as propylene, butene-1, 4-methyl-pentene-1, hexene-1, octene-1 or styrene; copolymers of such olefinic hydrocarbons, especially ethylene, with non hydrocarbon comonomers e.g. esters with olefinic groups such as vinyl esters e.g. vinyl acetate or alkyl(meth)acrylate or vinyl chloride may also be made. Addition polymerisation of iso olefins e.g. of 4–8 carbons such as isobutene alone or with other comonomers such as butadiene is included, as in addition polymerization of olefinic non hydrocarbon monomers such as vinyl esters e.g. of 3–20 carbons especially 4–10 carbons such as vinyl acetate and propionate, and alkyl(meth)acrylates wherein the alkyl group has 1–20 carbons, especially 1–4 carbons for solid polymers e.g. polymethyl methacrylate, and 4–20 carbons for polymers for use as pour point depressants and VI improvers e.g. polydodecyl acrylate and methacrylate and copolymers with 2–10 monomers of different alkyl chain lengths. Vinyl chloride homopolymers and copolymers e.g. with vinylidene chloride may also be made.

The method may also be used for ring opening reactions such as reactions of epoxides, episulphides or cyclic imines with organic compounds containing at least one active hydrogen such as compounds with at least one OH, NH or SH group, such as alcohols, phenols, primary or secondary amines or thiols. Alcohols e.g. of 1–30 carbons such as 2–6 carbons (e.g. butanol) especially alkanols or cycloalkanols are preferred. The epoxide is usually of 2–8 carbons e.g. ethylene oxide, propylene oxide, butylene oxide or cyclohexane oxide, while the episulphide and cyclic imines are preferably the corresponding analogues e.g. ethylene imine and ethylene sulphide.

In the case of polymerisation the method may be used to estimate the properties of the polymer made from the NIR spectrum of the feedstock (under constant conditions) or from the NIR spectrum of the product. Examples of properties are number and weight average molecular weights, and the molecular weight distribution, viscosity e.g. at 100° C., fluidity index, density, and chemical composition e.g. percentage of at least one monomer or comonomer in the polymer percentage of unsaturation e.g. ethylenic type, or side chain grouping, e.g. methyl, crystallinity, rigidity, flow parameters, draw strength at the flow threshold, free cracking resistance and shock resistance. In addition for polyisobutenes, the property may also be content of butene-1, and light and heavy polyisobutenes and unsaturation expressed in groups per liter and maleinisation index (or succinylation ratio) (sensitivity to Diels Alder reactions) as well as particular types of unsaturation e.g. vinylidene $CH_2=C—$ VIN, tri $(CH_3—C(CH_3)=CH<)$ TRII, tri 2 (TRI2) $(CH_3—CH=C—)$ TRITOT $(R—CH=C<)$, TETRA $(>C=C<)$. For polyolefins e.g. polyethylene, other properties include percentage of comonomer, volatile compounds and degree of conversion. For polyalkylenoxylated compounds e.g. ethylene oxide condensates e.g. with alcohols, the method may be used to monitor the degree of conversion or the amount of alkylene oxide consumed, as well as the quality of the product e.g. content of groups derived from at least one epoxide or the distribution of those groups in the polymer chain, the product weight and number average molecular weight and its distribution, proportions of low and high molecular weight products (e.g. 150–600 or 600–15000 such as 5000–12000 respectively) Hydroxyl index (or mean number of hydroxyl groups per molecule), percentage of primary secondary and tertiary hydroxyl groups, allylic or propylenic type unsaturation, or impurity content.

The method is of especially value in the polymerisation of ethylene alone or with at least one alpha olefin as described above. The process is usually catalysed by at least one transition metal catalyst especially of Group IVA, VA or VIA, of the Periodic Table, such as titanium, zirconium, vanadium and/or chromium. The catalysts may be organometallic (including π complexes), especially with the above transition metals, and may be in the presence of at least one organo aluminium cocatalyst as in Zeigler Natta catalysts. Non organometallic catalysts such as chromium oxide may be used. The catalyst may be unsupported or supported e.g. on silica and/or alumina.

The method may also be applied to organic chemical processes, which are not polymerisations (including oligomerisation); thus processes involving only monomeric starting materials and products are suitable. In particular these include processes in which at least one of a reactant and a product is a functionalised compound i.e. is not a hydrocarbon but contains at least one functional group, e.g. with at least one atom other than carbon and hydrogen, in particular at least one oxygen, nitrogen, sulphur, phosphorus, or halogen e.g. chlorine, bromine, iodine or fluorine atom, especially 1–3 such atoms in the compound. The functional group may be an alcohol, phenol, thiol, primary secondary or tertiary amine, aldehyde, ketone, ester, acid, amide, nitrile or ether or sulphide, or aromatic or aliphatic halide.

In particular the process may be a hydration such as an olefin to an alcohol (e.g. ethylene or propylene to ethanol or isopropanol respectively) dehydration such as an alcohol to an olefin (e.g. tert butanol to isobutene) etherification such as reaction of an alcohol or phenol with an olefin (e.g. tert butanol with isobutene to form Methyl tert butyl ether) or reaction of an olefin with water (e.g. ethylene to diethyl ether), esterification such as reaction of a carboxylic acid (or derivative thereof e.g. acid chloride) with an alcohol e.g. alkanol of 1–20 carbons) or with an olefin (e.g. ethylene, propylene or n or isobutene), such as reaction of acetic acid with ethylene to form ethyl acetate or with dehydrogenation) vinyl acetate. The process may also be an oxidation e.g. an alcohol or aldehyde to an acid such as methanol to formic acid, or a hydrocarbon to an alcohol or ketone or an acid e.g. naphtha to acetic acid or methane to formic acid or cumene to acetone and phenol, an ammoxidation e.g. an aliphatic substituted olefin (with optionally 3–6 carbons) to a nitrile such as propylene to acrylonitrile, or a carbonylation of an olefin or an alcohol to form a carboxylic acid and/or anhydride, such as the reaction of methanol with carbon monoxide to form acetic acid and/or anhydride.

In each of the above processes the property of a product determined or predicted by the method of the invention can be compared to the desired figure and notice taken of any deviations by adjusting the parameters of the process e.g. proportion or nature of feed and/or temperature/pressure etc to bring the property back to the desired figure. This control of the process, which may be a polymerization chemical process, is usually performed with a micro computer which is linked to the spectrometer and also performs the search for the standards $^s$m. The online control of the process is very efficient and very fast.

The present invention invention also provides an apparatus suitable for carrying out the method of the invention comprising an infra red spectrometer and a computer wherein the infra red spectrometer is linked to the computer program in such manner that the property may be determined continuously and in real time. The spectrometer is suitable for measuring spectra in the 600–2600 nm wavelength range (FIG. 3) and can be linked to a signal processing device to allow numerical treatment of the spectrum, preferably by Fourier transformation. The spectrometer receives at least one signal from a vessel containing product or from a feed or product line. The information obtained can be use an information vector for the computer which is programmed to determine the property or yield eg via calculations on the proximity indices in relation to standards. Conveniently in relation to a process, the computer may be used in a closed loop feed back control system for controlling processing equipment eg changing the process parameters in response to variations in the property and/or yield of product from the desired value, measurement of more than one absorption in the NIR spectrum of the product and/or feed.

The benefits of invention allow improvements in modelling with the following areas, identification and classification of novel products; simultaneous estimation of all of P properties on a sample without the need for generating P different models, and with the option of automatic upgrading of the model, the method being self learning or adjusting. The method of the invention overcomes the difficulties with the classical regressional approach, in particular avoiding all difficulties with numerical stability of the models, allowing easy and rapid identification and classification of a sample of a product analyzed by spectral recognition and then instant conclusions as to whether the sample is known or unknown, allowing simultaneous determination of many properties and whether the property is simply additive or synergetic in relation to a blend composition; the latter is particularly useful for different blend indices and the indices considered.

The method also allows an extension of the field of application of the method without the need to rewrite the model, apart from the need to integrate the new samples which are inside or outside the previous field of validity of the method. This possibility of automatic learning, which is not possessed by traditional regression techniques, is a decisive advantage in the framework of continuous inline industrial control processes, because it allows the return of the industrial plant operations to the model in a certain and rapid manner in a minimum time and with all the properties considered in the model. In contrast classical regression methods would necessitate the redevelopment of all the models, which is long and laborious without being able to guarantee the result of the new model obtained, because a new validation period is necessary; in addition during the redevelopment of the model any commercial use of the model in a plant is very limited. Furthermore, the topological method of invention allows equally the easy extension to a number of properties, which are simply incorporated into the known bank.

This remarkable possibility is true not only for conventional properties such as physical chemical and/or rheological properties, but also for complex ones. The methods of the invention equally allow application of the models from one apparatus to another and from one spectral region to another, where conventional regressive method cannot give satisfactory solutions. This apparatus portability is made possible by the fact that the differences between different spectra are the same in one apparatus as another, for the same type of spectrometer being considered (e.g. network scatter, Fourier transform, accousto optical system AOTS, diode array etc). This portability between spectral regions depends on the fact that as the spectral regions are intercorrelated, the relations between the spectra are maintained between one another.

The invention is illustrated in the following Examples in which the Minimal Index is calculated according to the Minimal Index Procedure described above. Mathematically the steps concerned are as follows.

For each couple of standard samples i, j, the Proximity Index $i_{ij}$ is determined from the NIR spectra by use of equation 1, 2, or 3 and the properties are measured. For each Proximity Index is calculated the absolute difference $EP_{ij}$ between the properties of the samples. The Minimal Index for property P is obtained from the average ($EM_pL$) of $EP_{ij}$ for different values of L when L≧ij. Thus the $EM_pL=1/K \Sigma \Sigma EP_{ij}$ for each of K samples for which ij≦L.

EMpL+t σ (M) is plotted against the proximity index and in addition there is plotted the reproducibility of the standard method, at a given level of confidence as defined in the Minimal Index Procedure above. The intercept of the curve from EMpL and the reproducibility give the upper limit for the Minimal Index.

For the Examples the data is expressed in Tables in a form as shown below in which the data is as follows.

| Proximity Index Wavelength λ | Weighting | Unknown | Estimated | Standard A | Standard B |
|---|---|---|---|---|---|
| cm$^{-1}$ | nm | | | | |
| Property l | | | | | |
| Property j | | | | | |
| Property m | | | | | |

The wavelengths chosen are shown in columns 1 and 2.

Column 3 gives the weight loading associated with each wavelength for the proximity index for the standards; 1 denotes no loading.

Column 4 shows for the unknown sample the absorption at the various wavelengths and at the bottom the properties of that sample determined by standard methods.

Column 5 shows for the unknown sample the estimated values of the properties and the absorptions using the method of the invention based on the properties and absorptions of the chosen standards.

Columns 6, 7 etc show the values of the absorptions and properties for the standards chosen from the bank.

Line 2 give the value of the proximity index between the unknown sample and each of the chosen standards.

EXAMPLE 1

On Line Determination of the Properties of Polybutenes in a Polyisobutene Plant

It is desired to control the properties of polybutenes made during their manufacture in order to adapt immediately the operating conditions to any changes in any product.

They were made by polymerisation of isobutene with an Bronsted acid catalyst to form a crude product from which distillation removes gaseous hydrocarbons and light polymeric products, and leaves heavy polyisobutene.

During the manufacture, the absorbances of heavy polyisobutene (Ref IA) were measured with an NIR spectrometer in the wavelength region 6000–8850 cm$^{-1}$. The spectrometer had been installed on line in a plant with the aid of a fast side loop situated in the line carrying the heavy polymer remaining after the distillation. An analyser attached to the spectrometer sent within 2 minutes to the controller of the plant a measure of the properties which had been obtained on the basis of the NIR spectrum measured on the above products and estimated using the method of the invention as follows.

The method chosen to treat the NIR spectrum involved a discrete selection of wavelengths chosen on the basis of chemical and/or statistical criteria, the chosen wavelength being between 6079 and 8803 cm.$^{-1}$. The absorbances were normalised according to procedure (2).

For a series of standard polyisobutene products, for which the NIR spectra were known, the Minimum Proximity Index was obtained by the method above to be 5×10$^{-6}$; this Index was not weighted. The proximity indices, between the absorbances of the standards in the bank and those of the unknown from the plant (normalised as above) were calculated and 5 standards 1B–1F were found with proximity indices<Min. Prox. Index.

By averaging the values of each property of those 5 standards it was possible to calculate the corresponding properties sought for the unknown for controlling the plant from knowing the viscosity at 100° C., the number average molecular weight (MN), size of the distribution of molecular weights obtained by gel permeation chromatography (called LGPC) as well as the content of butene-1 (BUT-1).

Other properties may also be determined such as density or inflammability point in a similar way.

Table 1.1 shows the results, from which it is clear that the calculated properties (in col 5) were all in agreement with those measured on the unknown by standard methods and were within the limits of reproducibility of those methods for use in the polyisobutene area (on the basis of a 95% probability in any measurement) namely 0.7% for viscosity (ASTM D445), 8.5° C. for inflammability point (ASTM D93-80), 5% for number average Molecular Weight and 3% for Molecular Weight distribution (both by Gel Permeation Chromatography), 10% for unsaturation (NMR) and for butene-1 (IR) and 1% for maleinisation index.

EXAMPLE 2

Determination of Properties of Low Molecular Weight Polyisobutene

The properties of a low molecular weight polyisobutene (2A) were determined in order to control its manufacturing unit as in Example 1. The method adopted was as in Example 1 with the absorbances of the polyisobutene measured as before in the 6000–8850 cm$^{-1}$ wavelength range with the aid of the NIR spectrometer installed on the residue line from the distillation unit.

The properties for determination were the viscosity at 100° C., the number average molecular weight, the LGPC (as in Ex.1), the content of butene-1, the inflammability point (IP) and the degree of unsaturation expressed in groups/liter, and the maleinisation index (PIBSA). The unsaturations were of the types VIN, TRII, TRI2, TRI2cis, TRI2trans, TRITotal and TETRA as defined above. The maleinisation index is particularly important for control of plants to make polyisobutenes as it is of great value to purchasers of low polyisobutenes.

The NIR spectra of a series of standard polyisobutenes whose properties were measured by reference techniques, were determined and from the bank obtained the Minimal Index was determined at 9×10$^{-5}$, via the unweighted proximity indices. The density of standards in the Bank was sufficiently high for there to be 5 standards 2B–2F inside the sphere with proximity indices with respect to the unknown less than the Minimal Index. By averaging the data from these standards, the properties of the unknown were determined. The results are shown in Table 2.1. Here also the properties of the polyisobutene from the plant calculated from the standards were all within the limits of reproducibility of the standard methods. Thus continuously and with total reliability, the quality of product from the plant can thus be obtained and can be maintained taking account of the process dynamics.

Other properties of the low molecular weight polyisobutene may be obtained in a similar way.

EXAMPLE 3

Determination of the Properties of a Polyethylene to Control its Manufacture

Ethylene was polymerised with a chromium catalyst in a plant to produce polyethylene, whose properties of density and fludity index (called grade) were to control its market specification. The product 3A, in the form of a powder, required rapid measurement of these properties to correct the plant operating conditions to ensure manufacture of a polymer of constant quality.

The NIR spectra of a series of standard polyethylenes were determined by means of a Fourier Transform NIR spectrometer in the 5500–8400 cm$^{-1}$ region, as well as their densities and fluidity indices to obtain a band of standards. The absorbances of the spectra were normalised as described above, to ensure better known numerical stability for the data. The Minimal Proximity Index was calculated from the unweighted proximity indices of the standards (according to Eq.2) and by means of the technique of Eq.8 in which v was 1.1, the proximity index to the product 3A was chosen at 0.015.

The proximity indices between the unknown polyethylene 3A from the plant and the standards were calculated according to Eq.2, and three standards 3B, 3C and 3D were found with small enough proximity indices. From the properties of these standards 3B–D by averaging, the properties of the unknown product 3A were obtained in less than 1 minute, allowing immediate reaction to all variations in the production operation. The results are shown in Table 3.1, and are in perfect agreement with the properties determined by reference methods, and within their reproducibilities, namely 1% for density and 14% for grade.

The method may be applied in the same way to the determination of other properties, for example percentage of comonomer in an ethylene copolymerisation, the degree of conversion of the reaction or the content of volatiles, as well as to other types of polymerisations to polyethylene such as ones with Ziegler Natta catalysts.

EXAMPLE 4

Control of Polyisobutene Production

Figure 3:
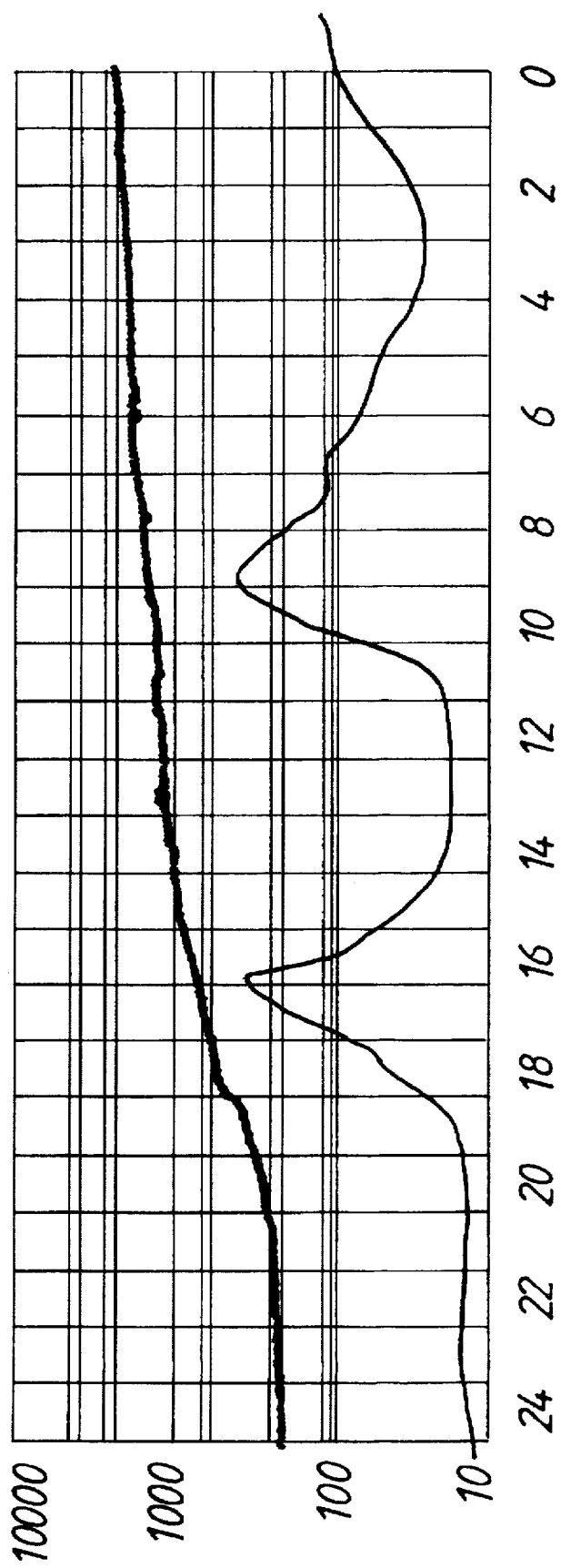

Polyisobutene production was monitored as described in Example 2 over a period of 24 hrs with a read out throughout of the calculated viscosity of the product heavy polymer. FIG. 3 shows this read out from the computer analysing the NIR data together with a copy of the spectrum of the product at the start of the 24 hr period when its properties were as follows: viscosity 2538 cps, Flash Pt 197° C., Mn 2267, Mol Wt Distrib. 1.93, % vinylidene 3.364, TRITOT 60.03, TRI2c 12.63, TRI2t 36.69% butene-1 2.65. Over this 24 hr period the viscosity changed significantly. The calculations to enable this to be followed continuously were possible by the method of this invention involving the remarkable property of the process of "automatic densification" and autoadjustment of the standards, with avoidance of the recalibrations and fastidious and uncertain remodellings of regressional methods. This aspect of the present method is described further below.

For many process operations involving on line analysis of product leaving the reactor, there may be only a few standards involving NIR absorbances on these products of known analysis or properties.

For a polyisobutene pilot plant, the absorbances of the standards for the products, were measured with an FTIR spectrometer between 6400–9000 cm$^{-1}$ and the properties were the percentages of constituents leaving the reactor as measured by distillation (i.e. the heavy and light fractions); these parameters were measured because they represent the most interesting to follow for the progress of the reaction, though others could also be used as well or instead if desired. The Minimal Index was calculated from the proximity indices of the standards (according to Eq.3) weighted here by the accuracy factor in absorptions at each wavelength chosen; the proximity index as with respect to the unknown was fixed by Procedure 3 at 3×10$^{-3}$. Because of the low population of standards in the band with proximity indices with respect to an unknown polyisobutene 4A from the unit within this level, no standards were found and hence no values can be directly estimated for the properties (shown as a question mark in col.5 of Table 4.1 hereafter with the rest of the absorbances of the unknown and those of 3 nearby standards 4B, 4C and 4D.

The densification process of procedure 2 was thus invoked in order to increase the bank of known standards. Tables 4.2 and 4.3 (in col.3) show the results obtained for "standards" MC1 and MC2 respectively determined by calculation and located with small enough proximity indices of process Eq. 3. Col 4 and later columns give the absorbances and properties of the existing standards of the bank used to generate novel "standards" namely 4B, 4C and 4E (for MC1) and 4B, 4D and 4E (for MC2). Col 2 gives for each of the novel standards the fraction from the known standards used in the mixture to generate the new ones. This fraction can be negative or positive but can be applied as in Eq.4.

Based on the new "standards" MC1 and MC2 (with Proximity Indices with respect to the unknown of 2.7×10$^{-3}$ and 2.6×10$^{-3}$ respectively), the properties of the unknown 4A were then calculated, by use of arithmetic averaging with results as shown in Table 4.4. The weight percentage of the 2 polymeric components in product 4A were well compatible with the measured values from the distillation in the light of the errors in the reproducibility of the latter.

The above process enables immediate auto adjustment of the bank by automatic incorporation of the novel "standards" as though they were originally measured ones. Thus property is remarkable as it enables determination of properties of products hitherto unknown in the bank and to gain precious time in the adjustment of operating conditions on the plant to take account of changes.

This autoadjustment process was used in a process whose results were as given in Table 4.5 below, which shows that the novel "standard" measured immediately after incorporation of the "standard" unrecognised in the bank is now recognised and can be used to calculate well all the properties and without any modification nor intervention from existing models. This operation is better than that of classical regressional models, which are incapable of predicting the properties of samples not included in the trial area or of predicting them with a non acceptable error; these regression techniques would require for use the preparation of new models for each property and without guarantee of success and the production unit using the new model would be operating blind during the recalibration period.

EXAMPLE 5

Determination of the Properties of a Polyethylene Glycol

A polyalkoxylenated product had been made discontinuously by polymerisation in the liquid phase of one or more epoxides specifically ethylene oxide with an organic compound possessing at least one active hydrogen atom, such as an alcohol specifically butanol. The values of the properties of the product during the process had hitherto been regularly evaluated in the laboratory by standard methods during the production in order to determine the necessary amounts of epoxide. However, the times to obtain the analytical results were generally prohibitive in terms of the amounts of epoxide consumed and quality of product obtained during non optimum operations.

The method of the present invention was applied to this process. A band of standards for polyethylenoxylated butanols covering the field between low ones (Mol. Wt about 200) up to high ones (Mol. Wt. of the order of 9000) was generated incorporating the properties of a number of these compounds as well as their spectra, determined in the 4000–8400 cm$^{-1}$ wavelength region with an FT NIR spectrometer. The properties considered were the hydroxyl index (fundamental for the conduct/progress of the reaction) as well as the viscosity measured at 100° C. and the molecular weight.

The bank of data was applied by the method of the invention to the production of a polyethylenoxylated butanol of Molecular Weight of about 8000 (PEG 8000). From the standards with spectra normalised per Eq.3 the Minimal Index was calculated at $1.2 \times 10^{-4}$. The Proximity Indices between the unknown PEG 8000 and the standards were calculated (using Eq. 2) and four standards 5A, 5B, 5C and 5D were found with Proximity Index values less than the Minimal Index. From the properties of these standards, the properties of the unknown PEG 8000 were calculated by averaging with (as shown in Table 5.1) excellent results for all which were obtained in less than 1 minute, enabling maintenance or immediate correction of the level of ethylene oxide used in order to maintain the final quality of the products. Furthermore the differences obtained between the results obtained by the above calculations and by standard methods were all inside the limits of reproducibility of those reference methods, namely 0.7% for the viscosity (by ASTM D445) and 5.8% and 3.6% respectively for the hydroxyl index below and above 100 (ASTM D4274). The Molecular Weight was obtained directly from the hydroxyl index with the same reproducibility values.

Other properties of the polyethylene oxylated butanol may be obtained in a similar way.

TABLE 1

| | | | | | | | | | |
|---|---|---|---|---|---|---|---|---|---|
| On line Determination of the Properties of a High MW Polyisobutene | | | | | | | | | |
| Prox. Index Wavelength | | | | | 1B | 1C | 1D | 1E | 1F |
| λ (cm-1) | λ (nm) | Wt | 1A Measured | Estimated | 2,28E-07 | 2,41E-07 | 3,17E-07 | 4,99E-07 | 5,05E-07 |
| 6079 | 1645 | 1 | 0,034526 | 0,0345348 | 0,03445 | 0,034579 | 0,034566 | 0,034566 | 0,034513 |
| 6109 | 1637 | 1 | 0,033387 | 0,0334816 | 0,033343 | 0,033452 | 0,033511 | 0,033514 | 0,033588 |
| 6165 | 1622 | 1 | 0,031521 | 0,0316246 | 0,031567 | 0,031568 | 0,031642 | 0,031691 | 0,031655 |
| 6200 | 1613 | 1 | 0,029482 | 0,0295274 | 0,029529 | 0,029419 | 0,029577 | 0,029578 | 0,029534 |
| 6215 | 1609 | 1 | 0,028092 | 0,0281402 | 0,028072 | 0,028047 | 0,028148 | 0,028212 | 0,028222 |
| 6262 | 1597 | 1 | 0,022757 | 0,0227916 | 0,022708 | 0,02274 | 0,022487 | 0,0228 27 | 0,022813 |
| 6418 | 1558 | 1 | 0,009918 | 0,0099332 | 0,009884 | 0,009823 | 0,010043 | 0,009945 | 0,009971 |
| 6532 | 1531 | 1 | 0,008198 | 0,0082184 | 0,008228 | 0,008124 | 0,008355 | 0,008288 | 0,008097 |
| 6649 | 1504 | 1 | 0,013928 | 0,0139594 | 0,013956 | 0,013878 | 0,01398 | 0,014021 | 0,013962 |
| 6698 | 1493 | 1 | 0,018189 | 0,0181368 | 0,018174 | 0,018078 | 0,018188 | 0,018186 | 0,018058 |
| 6821 | 1466 | 1 | 0,023312 | 0,0233096 | 0,023296 | 0,023313 | 0,02329 | 0,023 32 | 0,023329 |
| 6901 | 1449 | 1 | 0,03066 | 0,03061 | 0,030665 | 0,030627 | 0,030622 | 0,03062 | 0,030516 |
| 6925 | 1444 | 1 | 0,032947 | 0,0329416 | 0,032984 | 0,032945 | 0,032842 | 0,032927 | 0,03301 |
| 6964 | 1436 | 1 | 0,034095 | 0,0340834 | 0,034175 | 0,034129 | 0,03404 | 0,034121 | 0,033952 |
| 6998 | 1429 | 1 | 0,033036 | 0,0330732 | 0,033113 | 0,033051 | 0,033061 | 0,033057 | 0,033084 |
| 7052 | 1418 | 1 | 0,037285 | 0,0373202 | 0,037367 | 0,037376 | 0,037 25 | 0,037374 | 0,037234 |
| 7062 | 1416 | 1 | 0,038945 | 0,0389808 | 0,039025 | 0,039019 | 0,038891 | 0,038957 | 0,039012 |
| 7092 | 1410 | 1 | 0,042821 | 0,0429034 | 0,042882 | 0,042993 | 0,042821 | 0,042866 | 0,042955 |
| 7148 | 1399 | 1 | 0,050224 | 0,0501864 | 0,050162 | 0,050204 | 0,05023 | 0,050197 | 0,050139 |
| 7158 | 1397 | 1 | 0,05171 | 0,0516546 | 0,051583 | 0,051672 | 0,051573 | 0,051668 | 0,051777 |
| 7199 | 1389 | 1 | 0,055328 | 0,0552568 | 0,055321 | 0,055251 | 0,055274 | 0,055195 | 0,055243 |
| 7220 | 1385 | 1 | 0,055837 | 0,055829 | 0,055823 | 0,055857 | 0,055805 | 0,055755 | 0,055905 |

TABLE 1-continued

On line Determination of the Properties of a High MW Polyisobutene

| Wavelength $\lambda$ (cm-1) | Prox. Index $\lambda$ (nm) | Wt | 1A Measured | 1A Estimated | 1B 2,28E-07 | 1C 2,41E-07 | 1D 3,17E-07 | 1E 4,99E-07 | 1F 5,05E-07 |
|---|---|---|---|---|---|---|---|---|---|
| 7231 | 1383 | 1 | 0,05578 | 0,0557724 | 0,055758 | 0,055782 | 0,055802 | 0,055606 | 0,055914 |
| 7262 | 1377 | 1 | 0,053775 | 0,053733 | 0,053785 | 0,053713 | 0,0538 | 0,053595 | 0,053772 |
| 7294 | 1371 | 1 | 0,048604 | 0,0484784 | 0,048495 | 0,048516 | 0,048501 | 0,048403 | 0,048477 |
| 7331 | 1364 | 1 | 0,040558 | 0,0405078 | 0,040492 | 0,040581 | 0,040499 | 0,040494 | 0,040473 |
| 7348 | 1361 | 1 | 0,036912 | 0,0368442 | 0,036891 | 0,036937 | 0,036791 | 0,036849 | 0,036753 |
| 7375 | 1356 | 1 | 0,028832 | 0,028823 | 0,028885 | 0,028916 | 0,028736 | 0,028825 | 0,028753 |
| 7402 | 1351 | 1 | 0,01934 | 0,0193446 | 0,019389 | 0,019411 | 0,019293 | 0,019343 | 0,019287 |
| 7899 | 1266 | 1 | 0,002143 | 0,0020506 | 0,002127 | 0,002037 | 0,002131 | 0,002039 | 0,001919 |
| 8000 | 1250 | 1 | 0,006563 | 0,0066608 | 0,00675 | 0,006643 | 0,006601 | 0,006705 | 0,006605 |
| 8097 | 1235 | 1 | 0,017014 | 0,0170314 | 0,016928 | 0,017022 | 0,01693 | 0,017118 | 0,017159 |
| 8197 | 1220 | 1 | 0,033957 | 0,033925 | 0,033887 | 0,033884 | 0,033837 | 0,034041 | 0,033976 |
| 8217 | 1217 | 1 | 0,037243 | 0,0373344 | 0,037337 | 0,037276 | 0,037258 | 0,037459 | 0,037342 |
| 8251 | 1212 | 1 | 0,043473 | 0,043491 | 0,043447 | 0,043397 | 0,043469 | 0,043609 | 0,043533 |
| 8278 | 1208 | 1 | 0,048882 | 0,0488738 | 0,048886 | 0,048835 | 0,048753 | 0,04903 | 0,048892 |
| 8333 | 1200 | 1 | 0,080806 | 0,080871 | 0,080945 | 0,080719 | 0,080878 | 0,080894 | 0,080919 |
| 8361 | 1196 | 1 | 0,0924 | 0,0924876 | 0,092499 | 0,092582 | 0,092447 | 0,092511 | 0,092399 |
| 8375 | 1194 | 1 | 0,091802 | 0,0918924 | 0,091893 | 0,091891 | 0,091957 | 0,091803 | 0,091918 |
| 8382 | 1193 | 1 | 0,090957 | 0,090951 | 0,090973 | 0,090952 | 0,090913 | 0,090875 | 0,091042 |
| 8403 | 1190 | 1 | 0,088076 | 0,0879942 | 0,087981 | 0,088052 | 0,088113 | 0,087893 | 0,087945 |
| 8418 | 1188 | 1 | 0,086503 | 0,0865104 | 0,086496 | 0,086468 | 0,086638 | 0,086372 | 0,086578 |
| 8503 | 1176 | 1 | 0,068153 | 0,0681298 | 0,068144 | 0,068087 | 0,06819 | 0,068083 | 0,068145 |
| 8540 | 1171 | 1 | 0,058772 | 0,0587116 | 0,058757 | 0,058746 | 0,058828 | 0,058655 | 0,058572 |
| 8598 | 1163 | 1 | 0,043961 | 0,0439804 | 0,043948 | 0,043992 | 0,043996 | 0,043947 | 0,044019 |
| 8658 | 1155 | 1 | 0,035651 | 0,0355848 | 0,035646 | 0,035571 | 0,03557 | 0,035569 | 0,035568 |
| 8703 | 1149 | 1 | 0,031642 | 0,0315346 | 0,03152 | 0,031638 | 0,031491 | 0,031545 | 0,031479 |
| 8726 | 1146 | 1 | 0,02824 | 0,028269 | 0,028194 | 0,02837 | 0,028297 | 0,028232 | 0,028252 |
| 8803 | 1136 | 1 | 0,013764 | 0,0137152 | 0,013641 | 0,013837 | 0,013715 | 0,013645 | 0,013738 |
| VISCOSITY | | | 4717 | 4708,2 | 4669 | 4783 | 5005 | 4484 | 4600 |
| MN | | | 2991 | 3031,4 | 3026 | 3016 | 3214 | 2930 | 2971 |
| LGPC | | | 1,81 | 1,812 | 1,80 | 1,82 | 1,78 | 1,84 | 1,82 |
| BUT-1 | | | 1,68 | 1,6298 | 1,62 | 1,4 | 1,669 | 1,66 | 1,8 |

In this Table 1.56E-07 means $1.56 \times 10^{-7}$

TABLE 2.1

On line Determination of the Properties of a Polyisobutene of Low Mol. Wt.

| λ (cm-1) | λ (nm) | Wt | 2A Measured | 2A Estimated 4,34E-07 | 2B 2,28E-07 | 2C 8,65E-07 | 2D 9,18E-07 | 2E 1,07E-06 | 2F 1,68E-06 |
|---|---|---|---|---|---|---|---|---|---|
| 6079 | 1645 | 1 | 0,03487 | 0,0350224 | 0,034809 | 0,035165 | 0,034927 | 0,03502 | 0,035191 |
| 6109 | 1637 | 1 | 0,033505 | 0,0336706 | 0,033428 | 0,033829 | 0,033536 | 0,033725 | 0,033835 |
| 6165 | 1622 | 1 | 0,029642 | 0,0296054 | 0,029568 | 0,029806 | 0,029475 | 0,029625 | 0,029553 |
| 6200 | 1613 | 1 | 0,026851 | 0,02668 | 0,026667 | 0,026958 | 0,026525 | 0,026706 | 0,026544 |
| 6215 | 1609 | 1 | 0,025316 | 0,025199 | 0,025198 | 0,025414 | 0,025055 | 0,025241 | 0,025087 |
| 6262 | 1597 | 1 | 0,020251 | 0,0201638 | 0,020177 | 0,020325 | 0,020046 | 0,020202 | 0,020069 |
| 6418 | 1558 | 1 | 0,008942 | 0,00905 | 0,009014 | 0,009098 | 0,009048 | 0,009074 | 0,009016 |
| 6532 | 1531 | 1 | 0,007916 | 0,0080262 | 0,007969 | 0,008029 | 0,008046 | 0,008052 | 0,008035 |
| 6649 | 1504 | 1 | 0,014038 | 0,0141226 | 0,014057 | 0,014102 | 0,014121 | 0,014208 | 0,014125 |
| 6698 | 1493 | 1 | 0,01827 | 0,0183048 | 0,018253 | 0,01832 | 0,018273 | 0,018369 | 0,018309 |
| 6821 | 1466 | 1 | 0,023637 | 0,0236528 | 0,023648 | 0,023639 | 0,023669 | 0,023643 | 0,023665 |
| 6901 | 1449 | 1 | 0,030691 | 0,0307184 | 0,030767 | 0,030664 | 0,030755 | 0,030708 | 0,030698 |
| 6925 | 1444 | 1 | 0,033186 | 0,0331576 | 0,033188 | 0,033115 | 0,033189 | 0,033208 | 0,033088 |
| 6964 | 1436 | 1 | 0,035052 | 0,0350774 | 0,03513 | 0,034983 | 0,035168 | 0,035051 | 0,035085 |
| 6998 | 1429 | 1 | 0,034516 | 0,0345532 | 0,034541 | 0,034482 | 0,034606 | 0,034506 | 0,034637 |
| 7052 | 1418 | 1 | 0,039698 | 0,0396944 | 0,039673 | 0,039522 | 0,039765 | 0,039724 | 0,039788 |
| 7062 | 1416 | 1 | 0,041541 | 0,0415304 | 0,041504 | 0,041347 | 0,041604 | 0,041588 | 0,041609 |
| 7092 | 1410 | 1 | 0,045553 | 0,0455686 | 0,045523 | 0,045335 | 0,045654 | 0,045617 | 0,045714 |
| 7148 | 1399 | 1 | 0,052377 | 0,052487 | 0,052493 | 0,052322 | 0,052627 | 0,052425 | 0,052568 |
| 7158 | 1397 | 1 | 0,053934 | 0,0539828 | 0,054005 | 0,053795 | 0,054148 | 0,053874 | 0,054092 |
| 7199 | 1389 | 1 | 0,056865 | 0,0569614 | 0,05701 | 0,056767 | 0,057037 | 0,056838 | 0,057155 |
| 7220 | 1385 | 1 | 0,056997 | 0,056996 | 0,057043 | 0,056965 | 0,057052 | 0,056858 | 0,057062 |
| 7231 | 1383 | 1 | 0,056741 | 0,0566584 | 0,056674 | 0,056626 | 0,056695 | 0,056527 | 0,05677 |
| 7262 | 1377 | 1 | 0,053595 | 0,0535546 | 0,053611 | 0,053499 | 0,053576 | 0,053515 | 0,053572 |
| 7294 | 1371 | 1 | 0,047392 | 0,0473396 | 0,047407 | 0,047357 | 0,047322 | 0,047342 | 0,04727 |
| 7331 | 1364 | 1 | 0,039219 | 0,039141 | 0,039245 | 0,039188 | 0,039132 | 0,039186 | 0,038954 |
| 7348 | 1361 | 1 | 0,035369 | 0,0352522 | 0,035363 | 0,03534 | 0,035213 | 0,035285 | 0,03506 |
| 7375 | 1356 | 1 | 0,026707 | 0,026597 | 0,02671 | 0,026679 | 0,026544 | 0,026663 | 0,026426 |
| 7402 | 1351 | 1 | 0,017328 | 0,017232 | 0,017357 | 0,017328 | 0,017195 | 0,017258 | 0,017022 |
| 7899 | 1266 | 1 | 0,002464 | 0,0024384 | 0,00244 | 0,002455 | 0,002472 | 0,002381 | 0,002444 |
| 8000 | 1250 | 1 | 0,007208 | 0,007183 | 0,00719 | 0,007144 | 0,007244 | 0,007126 | 0,007215 |
| 8097 | 1235 | 1 | 0,017338 | 0,0172718 | 0,017276 | 0,01724 | 0,017281 | 0,017216 | 0,017346 |
| 8197 | 1220 | 1 | 0,035357 | 0,0352078 | 0,035245 | 0,035151 | 0,035316 | 0,034991 | 0,035336 |
| 8217 | 1217 | 1 | 0,039433 | 0,0393774 | 0,039449 | 0,039195 | 0,03959 | 0,039126 | 0,039527 |
| 8251 | 1212 | 1 | 0,047005 | 0,0468886 | 0,046848 | 0,046753 | 0,047075 | 0,046638 | 0,047129 |

TABLE 2.1-continued

On line Determination of the Properties of a Polyisobutene of Low Mol. Wt.

| λ (cm-1) | Prox. Index Wavelength λ (nm) | Wt | 2A Measured | 2A Estimated 4,34E-07 | 2B 2,28E-07 | 2C 8,65E-07 | 2D 9,18E-07 | 2E 1,07E-06 | 2F 1,68E-06 |
|---|---|---|---|---|---|---|---|---|---|
| 8278 | 1208 | 1 | 0,05312 | 0,0530672 | 0,053062 | 0,052878 | 0,053291 | 0,052931 | 0,053174 |
| 8333 | 1200 | 1 | 0,081058 | 0,0809726 | 0,081013 | 0,080977 | 0,080954 | 0,081039 | 0,080808 |
| 8361 | 1196 | 1 | 0,093478 | 0,093531 | 0,093501 | 0,093565 | 0,093469 | 0,093651 | 0,093469 |
| 8375 | 1194 | 1 | 0,094014 | 0,0941538 | 0,094091 | 0,094159 | 0,09414 | 0,094226 | 0,094153 |
| 8382 | 1193 | 1 | 0,093212 | 0,09345 | 0,093337 | 0,093337 | 0,093457 | 0,093559 | 0,09356 |
| 8403 | 1190 | 1 | 0,08976 | 0,0899258 | 0,089806 | 0,089808 | 0,089953 | 0,089966 | 0,090096 |
| 8418 | 1188 | 1 | 0,08678 | 0,0869858 | 0,086901 | 0,086907 | 0,086959 | 0,087037 | 0,087125 |
| 8503 | 1176 | 1 | 0,06419 | 0,0641896 | 0,064217 | 0,064345 | 0,064015 | 0,064341 | 0,06463 |
| 8540 | 1171 | 1 | 0,054912 | 0,0548696 | 0,054942 | 0,055027 | 0,054736 | 0,055017 | 0,054626 |
| 8598 | 1163 | 1 | 0,040824 | 0,0408046 | 0,04087 | 0,040884 | 0,040724 | 0,040918 | 0,040627 |
| 8658 | 1155 | 1 | 0,03355 | 0,0335614 | 0,033553 | 0,033718 | 0,033461 | 0,033613 | 0,033462 |
| 8703 | 1149 | 1 | 0,029161 | 0,0291404 | 0,029156 | 0,029278 | 0,029022 | 0,029172 | 0,029074 |
| 8726 | 1146 | 1 | 0,025375 | 0,025314 | 0,025338 | 0,025341 | 0,025223 | 0,025394 | 0,025205 |
| 8803 | 1136 | 1 | 0,011761 | 0,0116668 | 0,011764 | 0,011772 | 0,011618 | 0,011658 | 0,011522 |
| | Viscosity | | 225 | 224,6 | 221 | 237 | 213 | 209 | 243 |
| | MN | | 946 | 923 | 926 | 930 | 914 | 902 | 943 |
| | LGPC | | 1,59 | 1,594 | 1,58 | 1,63 | 1,55 | 1,62 | 1,59 |
| | VIN | | 0,02 | 0,0216 | 0,017 | 0,025 | 0,018 | 0,021 | 0,027 |
| | TRI1 | | 0,012 | 0,0112 | 0,01 | 0,009 | 0,01 | 0,017 | 0,01 |
| | TRI2 | | 0,41 | 0,407 | 0,411 | 0,405 | 0,425 | 0,414 | 0,38 |
| | TRI2c | | 0,112 | 0,1156 | 0,115 | 0,111 | 0,121 | 0,121 | 0,11 |
| | TRI2t | | 0,298 | 0,2914 | 0,296 | 0,294 | 0,304 | 0,293 | 0,27 |
| | TRItot | | 0,578 | 0,5766 | 0,586 | 0,557 | 0,594 | 0,598 | 0,548 |
| | TETRA | | 0,163 | 0,1686 | 0,159 | 0,177 | 0,17 | 0,17 | 0,167 |
| | BUT-1 | | 7,0 | 7,3 | 7,2 | 7,2 | 7,5 | 7,13 | 7,47 |
| | Flash Point | | 171 | 170 | 170 | 172 | 168 | 165 | 175 |
| | PIBSA | | 99 | 99,2 | 99,5 | 98,6 | 98,4 | 99,3 | 100,1 |

TABLE 3.1

Determination of the Properties of a Polyethylene to Control its Manufacture

| λ (cm-1) | Prox. Index Wavelength λ (nm) | Wt | 3A Measured | 3A Estimated 0,0042626 | 3B 0,0072895 | 3C 0,0095186 | 3D 0,012812 | 3E 0,017956 | 3F 0,020326 |
|---|---|---|---|---|---|---|---|---|---|
| 5520 | 1812 | 1 | 2,9479 | 2,96034 | 2,9491 | 2,9576 | 2,9467 | 2,99 | 2,9583 |
| 5532 | 1808 | 1 | 2,9677 | 2,98038 | 2,9708 | 2,978 | 2,9663 | 3,0081 | 2,9787 |
| 5544 | 1804 | 1 | 2,9663 | 2,97482 | 2,9668 | 2,9721 | 2,96 | 3,0018 | 2,9734 |
| 5556 | 1800 | 1 | 2,9003 | 2,90612 | 2,898 | 2,9034 | 2,891 | 2,9307 | 2,9075 |
| 5568 | 1796 | 1 | 2,7954 | 2,8019 | 2,7949 | 2,7982 | 2,7872 | 2,8221 | 2,8071 |
| 5580 | 1792 | 1 | 2,7574 | 2,76272 | 2,7576 | 2,7579 | 2,7484 | 2,7806 | 2,7691 |
| 5592 | 1788 | 1 | 2,8275 | 2,83096 | 2,827 | 2,8257 | 2,8166 | 2,848 | 2,8375 |
| 5604 | 1784 | 1 | 2,9641 | 2,96714 | 2,9628 | 2,9637 | 2,9534 | 2,9834 | 2,9724 |
| 5616 | 1781 | 1 | 3,1253 | 3,12946 | 3,1245 | 3,1266 | 3,1188 | 3,1432 | 3,1342 |
| 5628 | 1777 | 1 | 3,4014 | 3,40732 | 3,4035 | 3,4037 | 3,3982 | 3,4176 | 3,4136 |
| 5640 | 1773 | 1 | 3,9219 | 3,9267 | 3,9225 | 3,9257 | 3,9216 | 3,9356 | 3,9281 |
| 5700 | 1754 | 1 | 3,271 | 3,2721 | 3,2677 | 3,2734 | 3,2756 | 3,2707 | 3,2731 |
| 5712 | 1751 | 1 | 3,5186 | 3,5218 | 3,5101 | 3,5287 | 3,5403 | 3,519 | 3,5109 |

TABLE 3.1-continued

Determination of the Properties of a Polyethylene to Control its Manufacture

| Wavelength | Prox. Index | | 3A | | 3B | 3C | 3D | 3E | 3F |
|---|---|---|---|---|---|---|---|---|---|
| λ (cm-1) | λ (nm) | Wt | Measured | Estimated 0,0042626 | 0,0072 895 | 0,0095 186 | 0,0128 12 | 0,0179 56 | 0,0203 26 |
| 5724 | 1747 | 1 | 3,967 | 3,9723 | 3,958 | 3,9822 | 3,9968 | 3,9724 | 3,9521 |
| 5736 | 1743 | 1 | 4,5291 | 4,5327 | 4,5232 | 4,5424 | 4,5574 | 4,5313 | 4,5092 |
| 5748 | 1740 | 1 | 5,4361 | 5,431 | 5,4283 | 5,4432 | 5,4697 | 5,4195 | 5,3943 |
| 5760 | 1736 | 1 | 6,2954 | 6,28316 | 6,2855 | 6,2961 | 6,3339 | 6,274 | 6,2263 |
| 5772 | 1733 | 1 | 6,1311 | 6,11846 | 6,1275 | 6,1305 | 6,1556 | 6,1092 | 6,0695 |
| 5784 | 1729 | 1 | 5,3685 | 5,36016 | 5,3687 | 5,3736 | 5,3895 | 5,3388 | 5,3302 |
| 5796 | 1725 | 1 | 4,7353 | 4,73128 | 4,7371 | 4,7434 | 4,7547 | 4,7058 | 4,7154 |
| 5808 | 1722 | 1 | 4,2184 | 4,21624 | 4,2189 | 4,22 | 4,2259 | 4,1997 | 4,2167 |
| 5820 | 1718 | 1 | 3,7382 | 3,7354 | 3,7383 | 3,7317 | 3,7329 | 3,7265 | 3,7476 |
| 5832 | 1715 | 1 | 3,2482 | 3,24516 | 3,252 | 3,2379 | 3,2325 | 3,2378 | 3,2656 |
| 5844 | 1711 | 1 | 2,7005 | 2,69712 | 2,7088 | 2,6865 | 2,6767 | 2,6865 | 2,7271 |
| 5856 | 1708 | 1 | 2,1677 | 2,16416 | 2,1782 | 2,1539 | 2,1453 | 2,1464 | 2,197 |
| 5868 | 1704 | 1 | 1,7811 | 1,777 | 1,7899 | 1,7685 | 1,7611 | 1,7578 | 1,8077 |
| 5880 | 1701 | 1 | 1,543 | 1,53756 | 1,549 | 1,5317 | 1,5247 | 1,5187 | 1,5637 |
| 5892 | 1697 | 1 | 1,386 | 1,37964 | 1,3902 | 1,3751 | 1,3678 | 1,362 | 1,4031 |
| 5904 | 1694 | 1 | 1,2531 | 1,24688 | 1,256 | 1,2422 | 1,2334 | 1,2363 | 1,2665 |
| 5916 | 1690 | 1 | 1,1365 | 1,1301 | 1,135 | 1,1265 | 1,1181 | 1,1269 | 1,144 |
| 8040 | 1244 | 1 | 2,017 | 2,00228 | 2,007 | 1,9968 | 1,9988 | 2,0068 | 2,002 |
| 8052 | 1242 | 1 | 2,1798 | 2,16904 | 2,1741 | 2,1633 | 2,1689 | 2,1757 | 2,1632 |
| 8064 | 1240 | 1 | 2,3554 | 2,3495 | 2,3502 | 2,3435 | 2,3506 | 2,3583 | 2,3449 |
| 8076 | 1238 | 1 | 2,5542 | 2,54602 | 2,5463 | 2,5412 | 2,5411 | 2,5583 | 2,5432 |
| 8088 | 1236 | 1 | 2,77 | 2,7631 | 2,764 | 2,7595 | 2,7549 | 2,778 | 2,7591 |
| 8100 | 1235 | 1 | 3,0086 | 3,00852 | 3,006 | 3,01 | 3,0001 | 3,0222 | 3,0043 |
| 8112 | 1233 | 1 | 3,2815 | 3,28462 | 3,281 | 3,2858 | 3,2755 | 3,2932 | 3,2876 |
| 8124 | 1231 | 1 | 3,5883 | 3,59138 | 3,5901 | 3,5889 | 3,5827 | 3,5958 | 3,5994 |
| 8136 | 1229 | 1 | 3,9312 | 3,932 | 3,9335 | 3,9321 | 3,9259 | 3,9335 | 3,935 |
| 8148 | 1227 | 1 | 4,3057 | 4,30886 | 4,3138 | 4,3117 | 4,3029 | 4,3088 | 4,3071 |
| 8160 | 1225 | 1 | 4,6904 | 4,70348 | 4,7083 | 4,7085 | 4,6972 | 4,7021 | 4,7013 |
| 8172 | 1224 | 1 | 5,0567 | 5,0748 | 5,0806 | 5,085 | 5,0706 | 5,0702 | 5,0676 |
| 8184 | 1222 | 1 | 5,3584 | 5,37704 | 5,3885 | 5,3897 | 5,3754 | 5,3703 | 5,3613 |
| 8196 | 1220 | 1 | 5,5454 | 5,56502 | 5,5766 | 5,5765 | 5,5653 | 5,5602 | 5,5465 |
| 8208 | 1218 | 1 | 5,5949 | 5,61744 | 5,6243 | 5,6316 | 5,6174 | 5,6161 | 5,5978 |
| 8304 | 1204 | 1 | 3,9622 | 3,97292 | 3,9776 | 3,9785 | 3,9664 | 3,9677 | 3,9744 |
| 8316 | 1203 | 1 | 3,7097 | 3,71178 | 3,7158 | 3,7128 | 3,7071 | 3,7087 | 3,7145 |
| 8328 | 1201 | 1 | 3,452 | 3,44774 | 3,4551 | 3,4456 | 3,4421 | 3,445 | 3,4509 |
| 8340 | 1199 | 1 | 3,1855 | 3,18512 | 3,1931 | 3,1844 | 3,1794 | 3,1793 | 3,1894 |
| 8352 | 1197 | 1 | 2,9428 | 2,94286 | 2,9445 | 2,9422 | 2,9419 | 2,9321 | 2,9536 |
| 8364 | 1196 | 1 | 2,7439 | 2,74022 | 2,7361 | 2,7369 | 2,7463 | 2,727 | 2,7548 |
| 8376 | 1194 | 1 | 2,6033 | 2,60352 | 2,5999 | 2,603 | 2,6104 | 2,5913 | 2,613 |
| 8388 | 1192 | 1 | 2,5465 | 2,55012 | 2,5457 | 2,553 | 2,5529 | 2,5426 | 2,5564 |
| 8400 | 1190 | 1 | 2,54 | 2,53978 | 2,5322 | 2,5348 | 2,5421 | 2,5409 | 2,5489 |
| 8412 | 1189 | 1 | 2,4926 | 2,48966 | 2,4825 | 2,4746 | 2,4951 | 2,497 | 2,4991 |
| 8424 | 1187 | 1 | 2,3635 | 2,35776 | 2,3517 | 2,343 | 2,3666 | 2,3639 | 2,3636 |
| 8436 | 1185 | 1 | 2,1984 | 2,1897 | 2,1797 | 2,1783 | 2,2041 | 2,1911 | 2,1953 |
| 8448 | 1184 | 1 | 2,047 | 2,03806 | 2,0245 | 2,0367 | 2,0514 | 2,0337 | 2,044 |
| 8460 | 1182 | 1 | 1,9027 | 1,89284 | 1,8818 | 1,8996 | 1,9027 | 1,8872 | 1,8929 |
| 8472 | 1180 | 1 | 1,7662 | 1,75796 | 1,7562 | 1,7615 | 1,7655 | 1,7557 | 1,7509 |
| 8484 | 1179 | 1 | 1,6745 | 1,66826 | 1,6685 | 1,6682 | 1,6732 | 1,6694 | 1,662 |
| 8496 | 1177 | 1 | 1,6317 | 1,61862 | 1,6109 | 1,6228 | 1,6257 | 1,618 | 1,6157 |
| grade | | | 4,4 | 4,3 | 4,2 | 4,4 | 4,1 | 4,3 | 4,6 |
| density | | | 0,953 | 0,952 | 0,952 | 0,953 | 0,952 | 0,952 | 0,951 |

TABLE 4.1

Determination of Percentages of Products leaving the Reactor

| Wavelength | Prox. Index | | 4A | | 4B | 4C | 4D |
|---|---|---|---|---|---|---|---|
| λ (cm-1) | λ (nm) | Wt | Measured | Estimated 0,02713 | 0,0743 38 | 0,1120 8 | 0,1655 1 |
| 6460 | 1548 | 0,0046638 | 0,9506 | | 0,9167 | 0,8792 | 0,9062 |
| 6620 | 1511 | 01013811 | 1,6348 | ?? | 1,5991 | 1,5768 | 1,5894 |
| 6652 | 1503 | 0,010524 | 1,7998 | ?? | 1,7841 | 1,7564 | 1,7742 |
| 6711 | 1490 | 0,015252 | 2,2127 | ?? | 2,1896 | 2,1635 | 2,1819 |

TABLE 4.1-continued

Determination of Percentages of Products leaving the Reactor

| Wavelength | Prox. Index | | 4A | | 4B | 4C | 4D |
|---|---|---|---|---|---|---|---|
| λ (cm-1) | λ (nm) | Wt | Measured | Estimated 0,02713 | 0,0743 38 | 0,1120 8 | 0,1655 1 |
| 6730 | 1486 | 0,017726 | 2,3151 | ?? | 2,2957 | 2,2755 | 2,2865 |
| 6796 | 1471 | 0,0051909 | 2,8005 | ?? | 2,7882 | 2,7608 | 2,7702 |
| 6824 | 1465 | 0,0024562 | 2,8892 | ?? | 2,8978 | 2,8678 | 2,8806 |
| 6996 | 1429 | 0,10627 | 3,7694 | ?? | 3,7794 | 3,7851 | 3,8055 |
| 7028 | 1423 | 0,3675 | 4,8996 | ?? | 4,8146 | 4,9265 | 4,9319 |
| 7076 | 1413 | 0,18801 | 3,9273 | ?? | 3,9644 | 3,9211 | 3,9504 |
| 7150 | 1399 | 0,14604 | 4,1671 | ?? | 4,1628 | 4,1702 | 4,2177 |
| 7215 | 1386 | 0,27199 | 2,6157 | ?? | 2,6289 | 2,5755 | 2,638 |
| 7263 | 1377 | 0,40707 | 3,1178 | ?? | 3,1596 | 3,0514 | 3,0678 |
| 7344 | 1362 | 0,33437 | 1,6553 | ?? | 1,7027 | 1,5795 | 1,598 |
| 7465 | 1340 | 0,025072 | 0,4511 | ?? | 0,4291 | 0,3898 | 0,3988 |
| 7504 | 1333 | 0,33793 | 0,72 | ?? | 0,7664 | 0,6542 | 0,6631 |
| 8100 | 1235 | 0,79137 | 3,0971 | ?? | 3,0875 | 3,1733 | 3,2087 |
| 8250 | 1212 | 2,5858 | 6,5167 | ?? | 6,4577 | 6,689 | 6,7332 |
| 8332 | 1200 | 0,99957 | 7,0388 | ?? | 6,9601 | 7,1546 | 7,1455 |
| 8434 | 1186 | 0,52305 | 6,3714 | ?? | 6,5339 | 6,3954 | 6,3456 |
| 8592 | 1164 | 1,9117 | 4,3131 | ?? | 4,4163 | 4,2975 | 4,2704 |
| 8660 | 1155 | 0,65567 | 3,6575 | ?? | 3,7572 | 3,7107 | 3,7241 |
| 8710 | 1148 | 0,59466 | 5,0015 | ?? | 5,0538 | 5,0873 | 5,0805 |
| 8767 | 1141 | 0,61289 | 5,4292 | ?? | 5,3749 | 5,5012 | 5,4754 |
| 8796 | 1137 | 0,70638 | 5,5988 | ?? | 5,5164 | 5,6277 | 5,5518 |
| 8815 | 1134 | 0,58808 | 4,6706 | ?? | 4,5946 | 4,6884 | 4,6 |
| 8841 | 1131 | 0,34646 | 3,4155 | ?? | 3,3726 | 3,4198 | 3,3602 |
| 8860 | 1129 | 0,25736 | 2,8157 | ?? | 2,7751 | 2,8008 | 2,7556 |
| 8936 | 1119 | 0,19692 | 1,203 | ?? | 1,2403 | 1,1788 | 1,1695 |
| 8955 | 1117 | 0,17434 | 0,9454 | ?? | 0,9796 | 0,9423 | 0,9195 |
| Light Fraction | | | 12,85 | ?? | 16,99 | 12,24 | 12,39 |
| Heavy Fraction | | | 42,71 | ?? | 36,19 | 41,94 | 40,78 |

TABLE 4.2

New "Standard" MC1 obtained by Densification

| Fraction in the Mixture | | | | | |
|---|---|---|---|---|---|
| λ (cm-1) | λ (nm) | MC1 | 4B 0,888 | 4E 0,277 | 4C -0,165 |
| 6460 | 1548 | 0,94283 | 0,9167 | 0,9887 | 0,8792 |
| 6620 | 1511 | 1,632 | 1,5997 | 1,7026 | 1,5768 |
| 6652 | 1503 | 1,8099 | 1,7841 | 1,8607 | 1,7564 |
| 6711 | 1490 | 2,2102 | 2,1896 | 2,2483 | 2,1635 |
| 6730 | 1486 | 2,3157 | 2,2957 | 2,356 | 2,2755 |
| 6796 | 1471 | 2,7984 | 2,7882 | 2,8087 | 2,7608 |
| 6824 | 1465 | 2,9 | 2,8978 | 2,8877 | 2,8678 |
| 6996 | 1429 | 3,7874 | 3,7794 | 3,8116 | 3,7851 |
| 7028 | 1423 | 4,8919 | 4,8146 | 5,1604 | 4,9265 |
| 7076 | 1413 | 3,9441 | 3,9644 | 3,8653 | 3,9211 |
| 7150 | 1399 | 4,1768 | 4,1628 | 4,2177 | 4,1702 |
| 7215 | 1386 | 2,61 | 2,6289 | 2,5287 | 2,5755 |
| 7263 | 1377 | 3,1169 | 3,1596 | 2,9409 | 3,0514 |
| 7344 | 1362 | 1,6447 | 1,7027 | 1,4198 | 1,5795 |
| 7465 | 1340 | 0,43655 | 0,4291 | 0,4326 | 0,3898 |
| 7504 | 1333 | 0,70392 | 0,7664 | 0,474 | 0,6542 |
| 8100 | 1235 | 3,0909 | 3,0875 | 3,1509 | 3,1733 |
| 8250 | 1212 | 6,5248 | 6,4577 | 6,8378 | 6,689 |
| 8332 | 1200 | 7,0355 | 6,9601 | 7,3483 | 7,1546 |
| 8434 | 1186 | 6,4076 | 6,5339 | 5,9953 | 6,3954 |
| 8592 | 1164 | 4,3058 | 4,4163 | 3,9466 | 4,2975 |
| 8660 | 1155 | 3,6516 | 3,7572 | 3,3484 | 3,7107 |
| 8710 | 1148 | 4,9879 | 5,0538 | 4,8357 | 5,0873 |
| 8767 | 1141 | 5,4021 | 5,3749 | 5,5484 | 5,5012 |
| 8796 | 1137 | 5,5708 | 5,5164 | 5,7792 | 5,6277 |
| 8815 | 1134 | 4,6591 | 4,5946 | 4,8835 | 4,6884 |
| 8841 | 1131 | 3,4302 | 3,3726 | 3,6088 | 3,4198 |
| 8860 | 1129 | 2,8374 | 2,7751 | 3,0153 | 2,8008 |
| 8936 | 1119 | 1,2122 | 1,2403 | 1,1023 | 1,1788 |
| 8955 | 1117 | 0,96257 | 0,9796 | 0,8959 | 0,9423 |
| Light Fraction | | | 13,12 | 16,99 | 0,17 | 12,24 |
| Heavy Fraction | | | 42,11 | 36,19 | 60,98 | 41,94 |

TABLE 4.3

New "Standard" MC2 obtained by Densification

Fraction in the Mixture Wavelength

| λ (cm-1) | λ (nm) | MC2 | 4B 0,877 | 4E −0,136 | 4C 0,259 |
|---|---|---|---|---|---|
| 6460 | 1548 | 0,93678 | 0,9167 | 0,9062 | 0,9887 |
| 6620 | 1511 | 1,6278 | 1,5997 | 1,5894 | 1,7026 |
| 6652 | 1503 | 1,8053 | 1,7841 | 1,7742 | 1,8607 |
| 6711 | 1490 | 2,2059 | 2,1896 | 2,1819 | 2,2483 |
| 6730 | 1486 | 2,3126 | 2,2957 | 2,2865 | 2,356 |
| 6796 | 1471 | 2,796 | 2,7882 | 2,7702 | 2,8087 |
| 6824 | 1465 | 2,8975 | 2,8978 | 2,8806 | 2,8877 |
| 6996 | 1429 | 3,7842 | 3,7794 | 3,8055 | 3,8116 |
| 7028 | 1423 | 4,8882 | 4,8146 | 4,9319 | 5,1604 |
| 7076 | 1413 | 3,9406 | 3,9644 | 3,9504 | 3,8653 |
| 7150 | 1399 | 4,1696 | 4,1628 | 4,2177 | 4,2177 |
| 7215 | 1386 | 2,6017 | 2,6289 | 2,638 | 2,5287 |
| 7263 | 1377 | 3,1154 | 3,1596 | 3,0678 | 2,9409 |
| 7344 | 1362 | 1,6437 | 1,7027 | 1,598 | 1,4198 |
| 7465 | 1340 | 0,43413 | 0,4291 | 0,3988 | 0,4326 |
| 7504 | 1333 | 0,70472 | 0,7664 | 0,6631 | 0,474 |
| 8100 | 1235 | 3,0874 | 3,0875 | 3,2087 | 3,1509 |
| 8250 | 1212 | 6,5187 | 6,4577 | 6,7332 | 6,8378 |
| 8332 | 1200 | 7,0354 | 6,9601 | 7,1455 | 7,3483 |
| 8434 | 1186 | 6,42 | 6,5339 | 6,3456 | 5,9953 |
| 8592 | 1164 | 4,3145 | 4,4163 | 4,2704 | 3,9466 |
| 8660 | 1155 | 3,6558 | 3,7572 | 3,7241 | 3,3484 |
| 8710 | 1148 | 4,9937 | 5,0538 | 5,0805 | 4,8357 |
| 8767 | 1141 | 5,4062 | 5,3749 | 5,4754 | 5,5484 |
| 8796 | 1137 | 5,5797 | 5,5164 | 5,5518 | 5,7792 |
| 8815 | 1134 | 4,6687 | 4,5946 | 4,6 | 4,8835 |
| 8841 | 1131 | 3,4355 | 3,3726 | 3,3602 | 3,6088 |
| 8860 | 1129 | 2,84 | 2,7751 | 2,7556 | 3,0153 |
| 8936 | 1119 | 1,2142 | 1,2403 | 1,1695 | 1,1023 |
| 8955 | 1117 | 0,9661 | 0,9796 | 0,9195 | 0,8959 |
| Light Fraction | | 13,26 | 16,99 | 12,39 | 0,17 |
| Heavy Fraction | | 41,99 | 36,19 | 40,78 | 60,98 |

TABLE 4.4

Determination of Percentages of Product leaving Reactor based on New "Standards"

| Prox. Index Wavelength | | | 4A | | MC1 | MC2 |
|---|---|---|---|---|---|---|
| λ (cm-1) | λ (nm) | Wt | Measured | Estimated 0,0025577 | 0,00273 89 | 0,00264 36 |
| 6460 | 1548 | 0,0046638 | 0,9506 | 0,9398 | 0,94283 | 0,93678 |
| 6620 | 1511 | 0,013811 | 1,6348 | 1,6299 | 1,632 | 1,6278 |
| 6652 | 1503 | 0,010524 | 1,7998 | 1,8076 | 1,8099 | 1,8053 |
| 6711 | 1490 | 0,015252 | 2,2127 | 2,208 | 2,2102 | 2,2059 |
| 6730 | 1486 | 0,017726 | 2,3151 | 2,3142 | 2,3157 | 2,3126 |
| 6796 | 1471 | 0,0051909 | 2,8005 | 2,7972 | 2,7984 | 2,796 |
| 6824 | 1465 | 0,0024562 | 2,8892 | 2,897 | 2,9 | 2,8975 |
| 6996 | 1429 | 0,10627 | 3,7694 | 3,7858 | 3,7874 | 3,7842 |
| 7028 | 1423 | 0,3675 | 4,8996 | 4,8901 | 4,8919 | 4,8882 |
| 7076 | 1413 | 0,18801 | 3,9273 | 3,9424 | 3,9441 | 3,9406 |
| 7150 | 1399 | 0,14604 | 4,1671 | 4,1732 | 4,1768 | 4,1696 |
| 7215 | 1386 | 0,27199 | 2,6157 | 2,6058 | 2,61 | 2,6017 |
| 7263 | 1377 | 0,40707 | 3,1178 | 3,1162 | 3,1169 | 3,1154 |
| 7344 | 1362 | 0,33437 | 1,6553 | 1,6442 | 1,6447 | 1,6437 |
| 7465 | 1340 | 0,025072 | 0,4511 | 0,43534 | 0,43655 | 0,43413 |
| 7504 | 1333 | 0,33793 | 0,72 | 0,70432 | 0,70392 | 0,70472 |
| 8100 | 1235 | 0,79137 | 3,0971 | 3,0892 | 3,0909 | 3,0874 |
| 8250 | 1212 | 2,5858 | 6,5167 | 6,5218 | 6,5248 | 6,5187 |
| 8332 | 1200 | 0,99957 | 7,0388 | 7,0355 | 7,0355 | 7,0354 |

TABLE 4.4-continued

Determination of Percentages of Product leaving Reactor based on New "Standards"

| Prox. Index Wavelength | | | 4A | | MC1 | MC2 |
|---|---|---|---|---|---|---|
| λ (cm-1) | λ (nm) | Wt | Measured | Estimated 0,0025577 | 0,00273 89 | 0,00264 36 |
| 8434 | 1186 | 0,52305 | 6,3714 | 6,4138 | 6,4076 | 6,42 |
| 8592 | 1164 | 1,9117 | 4,3131 | 4,3101 | 4,3058 | 4,3145 |
| 8660 | 1155 | 0,65567 | 3,6575 | 3,6537 | 3,6516 | 3,6558 |
| 8710 | 1148 | 0,59466 | 5,0015 | 4,9908 | 4,9879 | 4,9937 |
| 8767 | 1141 | 0,61289 | 5,4292 | 5,4041 | 5,4021 | 5,4062 |
| 8796 | 1137 | 0,70638 | 5,5988 | 5,5752 | 5,5708 | 5,5797 |
| 8815 | 1134 | 0,58808 | 4,6706 | 4,6639 | 4,6591 | 4,6687 |
| 8841 | 1131 | 0,34646 | 3,4155 | 3,4329 | 3,4302 | 3,4355 |
| 8860 | 1129 | 0,25736 | 2,8157 | 2,8387 | 2,8374 | 2,84 |
| 8936 | 1119 | 0,19692 | 1,203 | 1,2132 | 1,2122 | 1,2142 |
| 8955 | 1117 | 0,17434 | 0,9454 | 0,96433 | 0,96257 | 0,9661 |
| Light Fraction | | | 12,85 | 13,19 | 13,12 | 13,26 |
| Heavy Fraction | | | 42,71 | 42,05 | 42,11 | 41,99 |

TABLE 4.5

Immediate use of new "Standard" by Autoadjustment

| Prox. Index Wavelength | | | | 4F | 4A pib13 |
|---|---|---|---|---|---|
| λ (cm-1) | λ (nm) | Wt | Measured | Estimated 0,0020232 | 0,0020 232 |
| 6460 | 1548 | 0,0046638 | 0,94974 | 0,9506 | 0,9506 |
| 6620 | 1511 | 0,013811 | 1,6313 | 1,6348 | 1,6348 |
| 6652 | 1503 | 0,010524 | 1,8058 | 1,7998 | 1,7998 |
| 6711 | 1490 | 0,015252 | 2,2127 | 2,2127 | 2,2127 |
| 6730 | 1486 | 0,017726 | 2,3113 | 2,3151 | 2,3151 |
| 6796 | 1471 | 0,0051909 | 2,7958 | 2,8005 | 2,8005 |
| 6824 | 1465 | 0,0024562 | 2,8874 | 2,8892 | 2,8892 |
| 6996 | 1429 | 0,10627 | 3,7659 | 3,7694 | 3,7694 |
| 7028 | 1423 | 0,3675 | 4,9065 | 4,8996 | 4,8996 |
| 7076 | 1413 | 0,18801 | 3,918 | 3,9273 | 3,9273 |
| 7150 | 1399 | 0,14604 | 4,1745 | 4,1671 | 4,1671 |
| 7215 | 1386 | 0,27199 | 2,6134 | 2,6157 | 2,6157 |
| 7263 | 1377 | 0,40707 | 3,1197 | 3,1178 | 3,1178 |
| 7344 | 1362 | 0,33437 | 1,654 | 1,6553 | 1,6553 |
| 7465 | 1340 | 0,025072 | 0,4501 | 0,4511 | 0,4511 |
| 7504 | 1333 | 0,33793 | 0,72137 | 0,72 | 0,72 |
| 8100 | 1235 | 0,79137 | 3,0929 | 3,0971 | 3,0971 |
| 8250 | 1212 | 2,5858 | 6,5384 | 6,5167 | 6,5167 |
| 8332 | 1200 | 0,99957 | 7,0344 | 7,0388 | 7,0388 |
| 8434 | 1186 | 0,52305 | 6,3814 | 6,3714 | 6,3714 |
| 8592 | 1164 | 1,9117 | 4,3249 | 4,3131 | 4,3131 |
| 8660 | 1155 | 0,65567 | 3,6709 | 3,6575 | 3,6575 |
| 8710 | 1148 | 0,59466 | 4,9942 | 5,0015 | 5,0015 |
| 8767 | 1141 | 0,61289 | 5,4319 | 5,4292 | 5,4292 |
| 8796 | 1137 | 0,70638 | 5,5822 | 5,5988 | 5,5988 |
| 8815 | 1134 | 0,58808 | 4,6679 | 4,6706 | 4,6706 |
| 8841 | 1131 | 0,34646 | 3,4061 | 3,4155 | 3,4155 |
| 8860 | 1129 | 0,25736 | 2,8072 | 2,8157 | 2,8157 |
| 8936 | 1119 | 0,19692 | 1,2042 | 1,203 | 1,203 |
| 8955 | 1117 | 0,17434 | 0,94588 | 0,9454 | 0,9454 |
| Light Fraction | | | | 12,55 | 12,85 | 12,85 |
| Heavy Fraction | | | | 43,35 | 42,71 | 42,71 |

TABLE 5.1

Determination of Properties of a PEG to control a Production Unit

| Wavelength | | | 5A | | 5B | 5C | 5D | 5E |
|---|---|---|---|---|---|---|---|---|
| | Prox. Index | | | | | | | 0,0001157 |
| λ (cm-1) | λ (nm) | Wt | Measured | Estimated 0,00006519 | 0,00000977 | 0,00007494 | 0,00010457 | 4 |
| 4164 | 2402 | 1 | 0,12662 | 0,121605 | 0,12559 | 0,1212 | 0,12117 | 0,11846 |
| 4308 | 2321 | 1 | 0,24254 | 0,2387275 | 0,24285 | 0,23781 | 0,23696 | 0,23729 |
| 4524 | 2210 | 1 | 0,054854 | 0,0567045 | 0,054802 | 0,056171 | 0,057599 | 0,058246 |
| 4836 | 2068 | 1 | 0,048031 | 0,0485855 | 0,048451 | 0,048238 | 0,048588 | 0,049065 |
| 5172 | 1933 | 1 | 0,059102 | 0,06188575 | 0,061585 | 0,061986 | 0,064102 | 0,05987 |
| 5436 | 1840 | 1 | 0,056088 | 0,0555625 | 0,056049 | 0,0555 | 0,055054 | 0,055647 |
| 5544 | 1804 | 1 | 0,068293 | 0,06745175 | 0,067773 | 0,066995 | 0,067073 | 0,067966 |
| 5748 | 1740 | 1 | 0,10824 | 0,107665 | 0,10872 | 0,10703 | 0,10673 | 0,10818 |
| 5856 | 1708 | 1 | 0,037196 | 0,0374255 | 0,037003 | 0,037603 | 0,037295 | 0,037801 |
| 6624 | 1510 | 1 | 0,014687 | 0,015498 | 0,014728 | 0,016063 | 0,01551 | 0,015691 |
| 6684 | 1496 | 1 | 0,019234 | 0,01960475 | 0,019068 | 0,019792 | 0,019826 | 0,019733 |
| 6720 | 1488 | 1 | 0,020139 | 0,02084475 | 0,020349 | 0,021013 | 0,020942 | 0,021075 |
| 6792 | 1472 | 1 | 0,027751 | 0,023453 | 0,022848 | 0023636 | 0,023758 | 0,02357 |
| 6972 | 1434 | 1 | 0,030389 | 0,03078325 | 0,030175 | 0,030929 | 0 03119 | 0,030839 |
| 7092 | 1410 | 1 | 0,021148 | 0,02166525 | 0,021221 | 0,022095 | 0,021621 | 0,021724 |
| 7146 | 1405 | 1 | 0,021822 | 0,02246175 | 0,02158 | 0,022824 | 0,02273 | 0,022713 |
| 7920 | 1263 | 1 | 0,004193 | 0,00522035 | 0,0042156 | 0,0057718 | 0,0054551 | 0,0054389 |
| 8172 | 1224 | 1 | 0,03318 | 0,0330015 | 0032074 | 0,032927 | 0,032945 | 0,03406 |
| 8352 | 1197 | 1 | 0,011492 | 0,0118575 | 0,010926 | 0,012427 | 0,011449 | 0,012628 |
| Hydroxyl Index | | | 13,1 | 13,1 | 13,1 | 13 | 13,2 | 13,15 |
| Viscosity | | | 701 | 704 | 703 | 710 | 708 | 695 |
| Molec. Weight | | | 8560 | 8612,5 | 8400 | 8370 | 8450 | 9230 |

We claim:

1. A method of determining or predicting a value $P_x$ of a property of a material which is a product of a process or is a feed to a process or a property of a product of a process from said material or yield of any of said processes, which method comprises measuring absorption $D_ix$ of said material at more than one wavelength in the region 600–2600 nm, comparing said absorptions or a derivative thereof with absorptions $D_im$ or derivatives thereof at the same wavelengths for a number of standards S in a bank, for which said property or yield P is known, and choosing from the bank at least one standard $S_m$ with property $P_m$ having the smallest average value of the absolute difference at each wavelength i between the absorption $D_ix$ (or derivative thereof) for the material and the absorption $D_im$ (or derivative thereof) for the standard $S_m$ to obtain value $P_x$ and, when more than one standard $S_m$ is chosen, averaging said properties or yields $P_m$ and wherein said process is at least one of a polymerization, an oligomerization or an organic reaction in which at least one of the reactant and a product is a functionalized compound.

2. A method according to claim 1 wherein a proximity index is defined by $i^2_{(xm)} = \Sigma (D_{ix}-D_{im})^2$, the proximity index being less than a minimal index $i_m$ which has been determined from preselected standards by (a) calculating for each pair of the standards a value of a corresponding proximity index to obtain a series of proximity indices with corresponding property differences, (b) relating values of the proximity indices to corresponding property differences (c) calculating an average of the corresponding property differences for predetermined values L which are greater than a corresponding proximity index, (d) calculating the minimal index based on the average property differences and a reproducibility standard for the property.

3. A method according to claim 1, wherein properties of synthetic standards, which are mixtures, and their spectra for consideration for possible choice for Sm are estimated from existing standards in the bank for which, in respect of each existing standard for use in said mixture equation (4) and (5) are met, $$\text{Min} Cj-uj \leq C_j \leq \text{Max } Cj+uj \quad (4)$$

and $\Sigma Cij=1$ wherein Cj is a fraction of component j in the sample i,

Min Cj is the minimum of j in the samples for which the method is to be used,

Max Cj is the maximum of j in the samples for which the method is to be used, and, uj is between 1.0 and 0.05.

4. A method according to claim 2 wherein the properties of the standards and spectra for consideration for possible choice are estimated by interpolation from measured properties of the standards and the spectra for which the proximity index with respect to an unknown is not more than 10 times the minimal index.

5. A method according to claim 3 wherein at least one of a) the estimated standards and the corresponding spectra, and b) the property $P_x$ of the unknown material and its spectrum, are added to the bank.

6. A method according to claim 1 wherein the property is a physicochemical property of material X.

7. A method according to claim 1 wherein the property is a physicochemical property or yield of a product of a process to which at least one material X is a feed.

8. A method according to claim 1 wherein said process is a polymerization.

9. A method according to claim 8 which is an addition polymerization of at least one unsaturated hydrocarbon, and the property to at least one of number and weight average molecular weight, molecular weight distribution, viscosity, viscosity index, fluidity index, density, chemical composition such as percentage of at least one monomer, or unsaturation of side chain group, crystallinity, rigidity, a flow property, draw strength at the flow threshold, cracking resistance and shock resistance.

10. A method according to claim 9, wherein the process is a polymerization of at least one alpha olefin of 2 8 carbons and the property is of the product and is at least one of the density, fluidity index, degree of conversion, content of volatiles and, in the case of copolymerization percentage of comonomer.

11. A method according to claim 9 wherein the process is a polymerization of isobutene and the property is of the product and is at least one of the viscosity, number average molecular weight, distribution of molecular weights, inflammability point, content of butene 1 unsaturation and maleinization index, and percentage of light and heavy fractions from distillation of the direct/product of the process.

12. A method according to claim 8 wherein the process is the polymerization reaction of an expoxide in the presence of an organic compound containing at least one hydroxy group and the property is at least one of the degree of conversion, and of the product, hydroxyl index, viscosity and molecular weight.

13. A method according to claim 1 wherein the process is a reaction in which at least one of a reactant and product is a functionalized compound, and is a hydration, dehydration, etherification, esterification, oxidation, ammonidation or carbonylation.

14. A method according to claim 1 which is computer implemented.

15. A computer programmed to perform the method of determining or predicting a value $P_x$ which is a value of a property of a material X, which is a product of a process or is a feed to a process or a property of a product of a process from said material or is a yield of any of said processes, which method comprises measuring the absorption $D_{ix}$ of said material at more than one wavelength in the region 600–2600 nm, comparing said absorptions or a derivative thereof with absorptions $D_{im}$ or derivatives thereof at the same wavelength for a number of standards S in a bank for which said property or yield P is known, and choosing from the bank at least one standard $S_m$ with property $P_m$, said standard having the smallest average value of the absolute difference at each wavelength i between the absorption $D_ix$ (or derivative thereof) for the material and the absorption $D_im$ (or derivative thereof) for the standard $S_m$ to obtain $P_x$, and, when more than one standard $S_m$ is chosen, averaging said properties or yields $P_m$, wherein said process is at least one of a polymerization, an oligomerization or an organic reaction in which at least one of the reactant and a product is a functionalized compound.

16. An apparatus suitable for use in the method of claim 1 which comprises an NIR spectrometer receiving at least one signal from a feed or product line in said process and being coupled to a computer to effect continuous measurement of the spectra of the feed and/or product and provide feed back control of the process.

17. A computer implemented method for a system including a spectrometer linked to a process line containing a material X, which is a product of a process or a feed to a process, a computer linked to the spectrometer, and a controller linked to the computer and the process line, the computer including databanks having stored therein absorptions of standard materials and corresponding properties of said materials, or of products of a process from said materials or yield of said process, the method comprises steps of:

measuring absorption at more than one wavelength in the region 600–2600 nm at the process line and producing absorption signals or derivatives thereof by the spectrometer in accordance therewith;

assessing the databanks of the computer in accordance with the absorption signals or derivatives thereof;

comparing, by the computer, the absorption signals or derivatives thereof to the absorptions of the standard materials stored in the databanks;

choosing at least one standard based on the comparing, said standard having the smallest average value of the absolute difference at each wavelength i between the absorption (or derivative thereof) for the material and the absorption (or derivative thereof) for the standards, with averaging of said properties or yields when more than one standard is chosen; and controlling said process line in accordance with the outputted property/yield wherein said process is at least one of a polymerisation, an oligomerisation or an organic reaction in which at least one of the reactant and a product is a functionalized compound.

* * * * *